(12) United States Patent
Gage et al.

(10) Patent No.: US 7,057,015 B1
(45) Date of Patent: Jun. 6, 2006

(54) HORMONE RECEPTOR FUNCTIONAL DIMERS AND METHODS OF THEIR USE

(75) Inventors: Fred H. Gage, La Jolla, CA (US); Steven T. Suhr, La Jolla, CA (US); Elad B. Gil, Boston, MA (US); Marie-Claude C. Senut, La Jolla, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 0 days.

(21) Appl. No.: 09/421,971

(22) Filed: Oct. 20, 1999

(51) Int. Cl.
  *C07K 14/00*  (2006.01)
  *C12N 15/00*  (2006.01)
  *C12N 15/12*  (2006.01)
  *C12N 15/63*  (2006.01)
  *C07H 21/04*  (2006.01)

(52) U.S. Cl. .................. 530/350; 435/69.1; 435/320.1; 435/325; 536/23.5

(58) Field of Classification Search ................ 530/350; 435/69.1, 320.1, 325; 536/23.5
See application file for complete search history.

(56) References Cited

U.S. PATENT DOCUMENTS

| | | | |
|---|---|---|---|
| 4,160,452 A | 7/1979 | Theeuwes | 128/260 |
| 4,256,108 A | 3/1981 | Theeuwes | 128/260 |
| 4,265,874 A | 5/1981 | Bonsen et al. | 424/15 |
| 4,394,448 A | 7/1983 | Szoka, Jr. et al. | 435/172 |
| 4,399,216 A | 8/1983 | Axel et al. | 435/6 |
| 4,405,712 A | 9/1983 | Vande Woude et al. | 435/5 |
| 4,619,794 A | 10/1986 | Hauser | 264/4.1 |
| 4,634,665 A | 1/1987 | Axel et al. | 435/68 |
| 4,650,764 A | 3/1987 | Temin et al. | 435/240 |
| 4,870,009 A | 9/1989 | Evans et al. | 435/70 |
| 4,952,496 A | 8/1990 | Studier et al. | 435/91 |
| 4,981,784 A * | 1/1991 | Evans et al. | 435/6 |
| 5,024,939 A | 6/1991 | Gorman | 435/69.1 |
| 5,252,479 A | 10/1993 | Srivastava | 435/235.1 |
| 5,399,346 A | 3/1995 | Anderson et al. | 424/93.21 |
| 5,599,904 A * | 2/1997 | Evans et al. | 530/350 |
| 5,830,462 A * | 11/1998 | Crabtree et al. | 424/93.21 |
| 6,265,173 B1 * | 7/2001 | Evans et al. | 435/7.1 |
| 6,268,158 B1 * | 7/2001 | Pantoliano et al. | 435/7.1 |

FOREIGN PATENT DOCUMENTS

| | | |
|---|---|---|
| WO | WO 89/05345 | 6/1989 |
| WO | WO 90/06997 | 6/1990 |
| WO | WO 92/05266 | 4/1992 |
| WO | WO 92/07573 | 5/1992 |
| WO | WO 92/14829 | 9/1992 |
| WO | WO 99/10510 | 3/1999 |

OTHER PUBLICATIONS

Aranda A, Pascual A. Nuclear hormone receptors and gene expression. Physiol Rev. 2001 Jul;81(3):1269-304.*
Lees JA et al. A 22-amino-acid peptide restores DNA-binding activity to dimerization-defective mutants of the estrogen receptor. Mol Cell Biol. Oct. 1990;10(10):5529-31.*
Peters GA, Khan SA. Estrogen receptor domains E and F: role in dimerization and interaction with coactivator RIP-140. Mol Endocrinol. Feb. 1999;13(2):286-96.*
Hutchens TW et al. Mol Endocrinol. Feb. 1990;4(2):255-67.*
*Apoptosis, The Molecular Basis of Cell Death*, Current Communications In Cell & Molecular Biology, Cold Spring Harbor Laboratory Press, 1991.
Bosselman et al., "Replication-Defective Chimeric Helper Proviruses and Factors Affecting Generation of Competent Virus: Expression of Moloney Murine Leukemia Virus Structural Genes via the Metallothionein Promoter" *Molecular and Cellular Biology* 7(5):1797-1806 (1987).
Brent and Ptashne, "A Eukaryotic Transcriptional Activator Bearing the DNA Specificity of a Prokaryotic Repressor," *Cell*, 43:729-736 (1985).

(Continued)

Primary Examiner—Joseph Murphy
(74) *Attorney, Agent, or Firm*—Foley & Lardner, LLP; Stephen E. Reiter

(57) ABSTRACT

The invention provides chimeric proteins having at least two functional protein units, each containing the dimerization domain of a member of the steroid/thyroid hormone nuclear receptor superfamily. The chimeric proteins can fold under crystallization conditions to form functional entities. The functional entities optionally contain a novel flexible peptide linker of variable lengths between at least two of the protein units. In a preferred embodiment, the linker is designed to be increased in increments of 12 amino acids each to aid in preparation of variant chimeric proteins. The DNA binding characteristics of the invention functional entities differ from those of wild-type complexes formed between "monomeric" receptors and their binding partners. Some functional entities, e.g. dimers expressed as fusion proteins, transactivate responsive promoters in a manner similar to wild-type complexes, while others do not promote transactivation and function instead essentially as constitutive repressors. The invention further provides nucleotide sequences encoding the invention chimeric proteins, cells containing such nucleotide sequences, and methods for using the invention chimeric proteins to modulate expression of one or more exogenous genes in a subject organism. In addition, isolated protein crystals suitable for x-ray diffraction analysis and methods for obtaining putative ligands for the invention chimeric proteins are provided.

19 Claims, 7 Drawing Sheets

OTHER PUBLICATIONS

Christopherson et al., "Ecdysteroid-dependent regulation of genes in mammalian cells by a *Drosophila* ecdysone receptor and chimeric transactivators"*Proc. Natl. Acad. Sci. USA*, 89:6314-6318 (1992).

Conaway and Conaway, 1994, "Transcription Mechanisms and Regulation", *Raven Press Series on Molecular and Cellular Biology,* vol. 3, Raven Press, Ltd., New York, NY.

Danos et al., "Safe and efficient generation of recombinant retroviruses with amphotropic and ecotropic host ranges" *Proc. Natl. Acad. Sci. USA* 85:6460-6464 (1988).

Devlin et al., "Random Peptide Libraries: A Source of Specific Protein Binding Molecules" *Science*, 249:404-406 (1990).

Evans R.M., "The Steroid and Thyroid Hormone Receptor Superfamily" *Science* 240:889-895 (1988).

Forman et al., "Identification of a Nuclear Receptor That Is Activated by Farnesol Metabolites" *Cell* 81:687-693 (1995).

Freedman et al., "The function and structure of the metal coordination sites within the glucocorticoid receptor DNA binding domain" *Nature* 334:543-546 (1988).

Friedmann, T., "Progress Toward Human Gene Therapy" *Science* 244:1275-1281 (1989).

Furth et al., "Temporal control of gene expression in transgenic mice by a tetracylcline-responsive promoter" *Proc. Natl. Acad. Sci. USA* 91: 9302-9306 (1994).

Giguere et al., "Identification of a receptor for the morphogen retinoic acid" *Nature* 330:624-629 (1987).

Glass et al., "Thyroid Hormone Receptor Binds with Opposite Transcriptional Effects to a Common Sequence Motif in Thyroid Hormone and Estrogen Response Elements" *Cell* 54:313-323 (1988).

Gossen et al., "Control of gene activity in higher eukaryotic cells by prokaryotic regulatory elements" *TIBS* 18:471-475 (1993).

Gossen et al., "Tight Control of gene expression in mammalian cells by tetracycline-responsive promoters" *Proc. Natl. Acad. Sci.* 89:5547-5551 (1992).

Gossen et al., "Transcriptional Activation by Tetracyclines in Mammalian Cells" *Science* 268:1766-1769 (1995).

Green and Chambon, "Nuclear receptor enhance our understanding of transcription regulation" *Trends Genet.* 4:309-314 (1988).

Green and Chambon, "Oestradiol induction of a glucocortiocoid-responsive gene by a chimaeric receptor" *Nature* 325:75-78 (1987).

Harrison, "A structural taxonomy of DNA-binding domains" *Nature* 353:715-719.

Hollenberg and Evans, "Multiple and Cooperative Trans-Activation Domains of the Human Glucocorticoid Receptor" *Cell* 55:899-906 (1988).

Jacobs and Michaels, "Zinc Finger Gene Database" *The New Biologist* 2(6):583 (1990).

Jacobs, G.H., "Determination of the base recognition positions of zinc fingers from sequence analysis" *The EMBO Journal* 11:4507-4517 (1992).

Jaenisch, R., "Transgenic Animals" *Science* 240:1468-1474 (1988).

Kamine et al., "Sp1-dependent activation of a synthetic promoter by human immunodeficiency virus type 1 Tat protein" *Proc. Natl. Acad. Sci. USA* 88:8510-8514 (1991).

Klock et al., "Oestrogen and glucocorticoid responsive elements are closely related but distinct" *Nature* 329:734-736 (1987).

Klug and Rhodes, 'Zince fingers': a novel protein motif for nucleic acid recognition *TIBS* 12:464-469 (1987).

Koelle et al., "The *Drosophila EcR* Gene Encodes an Ecdysone Receptor, a New Member of the Steroid Receptor Superfamily" *Cell* 67:59-77 (1991).

Kumar and Chambon, "The Estrogen Receptor Binds Tightly to its Responsive Element as a Ligand-Induced Homodimer" *Cell* 55:145-156 (1988).

Kumar et al., "Functional Domains of the Human Estrogen Receptor" *Cell* 51:941-951 (1987).

Ladias et al., "Regulation of the Apolipoprotein AI Gene by ARP-1, a Novel Member of the Steroid Receptor Superfamily" *Science* 251:561-565 (1991).

Lee et al., CD8 Surface Levels Alter the Fate of $\alpha/\beta$ T Cell Receptor-expressing Thymocytes in Transgenic Mice *J. Exp. Med.* 175:1013-1025 (1992).

Leonard et al., "Charaterization of Somatostatin Transactivating Factor-1, a Novel Homeobox Factor That Stimulates Somatostatin Expression in Pancreatic Islet Cells" *Molecular Endocrinology* 7(10):1275-1283.

Mangelsdorf et al., "The Retinoid Receptors" *The Retinoids: Biology, Chemistry, and Medicine, 2nd Edition* 8:319-349 (1994).

Markowitz, et al. "A Safe Packaging Line for Gene Transfer: Separating Viral Genes on Two Different Plasmids" *Journal of Virology* 61(4):1120-1124 (1988).

Miller et al., "Repetitive zinc-binding domains in the protein transcription factor IIIA from *Xenopus oocytes*" *The EMBO Journal* 4(6):1609-1614 (1985).

Miller, A. D., "Retrovirus Packaging Cells" *Human Gene Therapy* 1:5-14 (1990).

Miyajima et al. "Identification of two novel members of erbA superfamily by molecular cloning: the gene products of the two are highly related to each other" *Nucleic Acids Research* 16(23): 11057-11074 (1988).

Mlodzik et al., "The *Drosophila seven-up* Gene, a Member of the Steroid Receptor Gene Superfamily, Controls Photoreceptor Cell Fates" *Cell* 60:211-224 (1990).

Mulligan et al., "Synthesis of rabbit $\beta$-globin in cultured monkey kidney cells following infection with a SV40 $\beta$-globin recombinant genome" *Nature* 277:108-114 (1977).

Mulligan, R.C., "The Basic Science of Gene Therapy" *Science* 260:926-932 (1993).

Nakamura et al., "DNA Sequence of the Gene for the Outer Membrance Lipoprotein of *E. coli*: an Extremely AT-Rich Promoter" *Cell*, 18:1109-1117 (1979).

O'Gorman et al., "Recombinase-Mediated Gene Activation and Site-Specific Integration in Mammalian Cells" *Science* 251:1351-1355 (1991).

Perlmann et al., "Determinants for selective RAR and TR recognition of direct repeat HREs" *Genes & Devel.* 7:1411-1422 (1993).

Petkovich et al., "A human retinoic acid receptor which belongs to the family of nuclear receptors" *Nature* 330:444-450 (1987).

Ross et al. "Targeted expression of a toxin gene to adipose tissue: transgenic mice resistant to obesity" *Gene and Development* 7:1318-1324 (1983).

Scott and Smith, "Searching for Peptide Ligands with an Epitope Library" *Science* 249:386-390 (1990).

Scott et al., "The structure and function of the Homoeodomain" *Biochimica et Biophysica Acta* 989:25-48 (1989).

Severne et al., "Metal binding 'finger' structures in the glucocorticoid receptor defined by site-directed mutagenesis" *EMBO J.* 7(8):2503-2508 (1988).

Shackleford et al., "Construction of a clonable, infectious, and tumorigenic mouse mammary tumor virus provirus and a derivative genetic vector" *Proc. Natl. Acad. Sci. USA* 85:9655-9659 (1988).

Shockett et al., "A modified tetracycline-regulated system provides autoregulatory, inducible gene expression in cultured cells and transgenic mice" *Proc. Natl. Acad. Sci.* 92:6522-6526 (1995).

Sladek et al., "Liver-enriched transcription factor HNF-4 is a novel member of the steroid hormone receptor superfamily" *Genes & Development* 4:2353-2365 (1990).

Strähle et al., "Synergistic action of the glucocortiocoid receptor with transcription factors" *EMBO* 7 (11):3389-3395 (1988).

Studier et al., "[6] Use of T7 RNA Polymerase to Direct Expression of Clones Genes" *Methods in Enzymology* 185:60-89 (1990).

Thompson and Evans, " Trans-activation by thyroid hormone receptors: Functional parallels with steroid hormone receptors" *Proc. Natl. Acad. Sci. U.S.A.* 86:3494-3498. (1989).

Umesono and Evans, "Determinants of Target Gene Specificity for Steroid/Thyroid Hormone Receptors" *Cell* 57:1139-1146 (1989).

Umesono et al., "Retinoic acid and thyroid hormone induce gene expression through a common responsive element" *Nature* 336:262-265 (1988).

Underhill et al., "Constitutively Active Retinoid Receptors Exhibit Interfamily and Intrafamily Promoter Specificity" *Molecular Endocrinology* 8:274-285 (1994).

Urlaub et al., "Effect of Gamma Rays at the Dihydrofolate Reductase Locus: Deletions and Inversion" *Somatic Cell and Molecular Genetics* 12(6):555-566 (1986).

Wang et al., "COUP Transcription factor is a member of the steroid receptor superfamily" *Nature* 340:163-166 (1989).

Watanabe et al., "Construction of a Helper Cell Line for Avian Reticuloendotheliosis Virus Cloning Vectors" *Molecular and Cellular Biology* 3(12):2241-2249 (1983).

Wong et al., "Human GM-CSF: Molecular Cloning of the Complementary DNA and Purification of the Natural and Recombinant Proteins" *Science* 228:810-815 (1985).

Yamamoto, K.R., "Steroid Receptor Regulated Transcription of Specific Genes and Gene Networks" *Ann. Rev. Genet.* 19:209-252 (1985).

Yao et al., "*Drosophila ultraspiracle* Modulates Ecdysone Receptor Function via Heterodimer Formation" *Cell* 71:63-72 (1992).

Yao et al., "Functional ecdysone receptor is the product of EcR and *Ultraspriacle* genes" *Nature* 366:476-479 (1933).

* cited by examiner

R/U(N)E

E(N)R/U

| | | | | | | | | | | | |
|---|---|---|---|---|---|---|---|---|---|---|---|
| Individual | | T | T | A | STOP | | | M | D | T | K (SEQ ID NO:79) |
| | ... | ACG | ACT | GCA | TAG(SEQ ID NO: 76) | | | ATG | GAC | ACC | AAA ...(SEQ ID NO:77) |
| Fused | | T | T | G | P | T | G | P | M | D | T K (SEQ ID NO:80) |
| | | ACG | ACT | GGG | CCA | ACA | GGG | CCC | ATG | GAC | ACC AAA (SEQ ID NO:78) |

Tether
G  P  G  G  G  S  G  G  G  S  G  T (SEQ ID NO:15)
GGG CCA GGA GGT GGC TCC GGG GGA GGT TCA GGC ACA (SEQ ID NO:30)
TGT CCC GGT CCT CCA CCG AGG CCC CCT CCA AGT CCG (SEQ ID NO:31)

FIG. 1

Native Dimer

Disorganized

Endodimer

Trimer

Tetramer

Oligomer

HORMONE RECEPTOR FUNCTIONAL DIMERS AND METHODS OF THEIR USE

This invention was made with Government support under Grant No. PO1 AG-10435 awarded by the National Institute of Aging. The U.S. Federal Government has certain rights in the invention.

FIELD OF THE INVENTION

The present invention relates to methods in the field of recombinant DNA technology, and products related thereto. In a particular aspect, the invention relates to methods for modulating the expression of exogenous genes in mammalian or non-mammalian systems, and products useful therefor.

BACKGROUND OF THE INVENTION

It is known in the art to produce fusion proteins for a number of purposes. In some cases, the two protein units in the single polypeptide have two essentially independent activities. The most common example of this application is the fusion of marking proteins, such as GFP, to intracellular factors as a means of observing their localization and expression (see, for example, A. W. Kerrebrock et al., *Cell*, 83:247–56, 1995; H. G. Wang et al., *Cell*, 87:629–638, 1996). Creation of fusion proteins has also been used to prolong the half-life of a protein (see, for example, R. A. Hallewell, et al., *J. Biol. Chem.*, 264:5260–5268, 1989; T. P. Yao et al., *Cell*, 77:6372, 1992) as well as other uses (see, for example, T. Sano et al., *Proc Natl Acad Sci U.S.A.*, 89:1534–1538, 1992).

A more complicated application of protein fusion is the production of fusion proteins wherein the two protein units cooperate to achieve a biological function. In functional dimers, both proteins must fold and interact with each other appropriately. V. A. Garcia-Campayo et al. (*Nature Biotech*, 15:663–667, (1997)) have utilized a peptide linker to fuse gene subunits together into a single biologically active peptide. Neuhold and Wold, (*Cell*, 74:1033–1042, (1993)) have reported the fusion of two proteins into a single biologically active protein that binds DNA targets, wherein the protein units interact with each other to the exclusion of competing heterodimer partners. However, fusion of proteins with multiple functions has been more difficult to produce, for example, steroid/thyroid hormone nuclear receptors are complex, multifunctional proteins with, minimally, four interconnected yet separable functions: ligand binding, dimerization, DNA binding, and transactivation.

Steroid/thyroid hormone nuclear receptors are used in the field of genetic engineering as a tool for studying control of gene expression and to manipulate and control development and other physiological processes. For example, applications for regulated gene expression in mammalian systems include inducible gene targeting, overexpression of toxic and teratogenic genes, anti-sense RNA expression, and gene therapy (see, for example, R. Jaenisch, *Science* 240:1468–1474, 1988). For cultured cells, glucocorticoids and other steroids have been used to induce the expression of a desired gene.

As another means for controlling gene expression in mammalian systems, an inducible tetracycline regulated system has been devised and utilized in transgenic mice, whereby gene activity is induced in the absence of tetracycline and repressed in its presence (see, e.g, Gossen et al. *PNAS* 89:5547–5551, 1992; Gossen et al., *TIBS* 18:471–475, 1993; Furth et al., *PNAS* 91:9302–9306, 1994; and Shockett et al., *PNAS* 92:6522–6526, 1995). However, disadvantages of the inducible tetracycline system include the requirement for continuous administration of tetracycline to repress expression and the slow clearance of antibiotic from bone, a side-effect that interferes with regulation of gene expression. While this system has been improved by the recent identification of a mutant tetracycline repressor that acts conversely as an inducible activator, the pharmacokinetics of tetracycline may hinder its use during development when a precise and efficient "on-off" switch is essential (see, e.g., Gossen et al., *Science* 268:1766–1769, 1995).

Certain insect steroid/thyroid hormone nuclear receptors have also been studied. The *Drosophila melanogaster* ecdysone receptor (EcR) (M. R. Koelle et al., *Cell* 67:59–77, 1995) is unlike the estrogen, androgen, and other homodimeric vertebrate steroid hormone nuclear receptors because it requires a heterologous dimer partner for functional transactivation. The obligate dimer partner, the product of the ultraspiracle (Usp) gene (V. C. Henrich et al., *Nuc. Acids Res.* 18: 4143–4148, 1990; T. P. Yao et al., supra, 1992; T. P. Yao et al., *Nature* 366:476–479, 1993), is an insect homolog of the mammalian retinoid X receptor (RXR) proteins found in vertebrates and other mammalian species. RXRs have been characterized as regulatory dimer partners of many mammalian class II steroid/thyroid hormone nuclear receptors, such as the thyroid hormone receptors, the retinoic acid receptors, and the vitamin D receptor (reviewed in Mangelsdorf and Evans, *Cell* 83:841–850, 1995; D. J. Mangelsdorf et al., *Cell* 83: 835–839, 1995). RXR is also a dimer partner of EcR.

Usp and RXR share a significant degree of sequence homology and some functional similarities; however, in formation of heterodimers with EcR, RXR interacts differently than Usp. One primary difference is that formation of EcR+RXR heterodimers is more highly stimulated by the steroid ligand ecdysteroid muristerone A (murA) than by 20-hydroxyecdysone (20-Ec), while formation of EcR+Usp heterodimers is potently stimulated by 20-hydroxyecdysone (K. S. Christopherson et al., *Proc Natl Acad Sci USA* 89:6314–6318, 1982; H. E. Thomas et al., *Nature* 362: 471–475, 1993). A second difference is in the way that ligand promotes efficient formation of EcR+Usp and EcR+RXR heterodimer complexes and concomitant binding to ecdysone response elements (EcREs). MurA stimulates EcR+Usp binding of EcREs approximately 3 to 7-fold over levels without ligand, but EcR+RXR complexes are completely dependent on ligand for heterodimerization. Further EcR+RXR complexes bind to EcREs at only 10–40% the level of EcR+Usp complexes (Christopherson et al., supra 1982; Thomas et al., supra 1993; Yao et al., supra, 1992 & 1993). This suggests that the affinity of EcR for its natural dimer partner, Usp, is significantly greater than its affinity for RXR.

EcR has been studied for use in transgene regulation; however, its use for this purpose is complicated by the requirement for superphysiological levels of RXR protein to be coexpressed (No et al., supra 1997), presumably because of the comparatively low affinity of EcR for RXR as a dimer partner. Of the mammalian cell types heretofore examined, only the 293 cell line appears capable of supporting high level transactivation of EcR without added RXR (Christopherson et al., supra, 1982). The requirement for co-expression of RXR in most mammalian systems raises concerns that RXR will heterodimerize with endogenous mammalian class II steroid/thyroid hormone nuclear receptors, causing altered differentiation, growth, or fitness of transduced cells.

A number of ecdysone receptors are known in the art as being a gene sequence responsive to an applied exogenous chemical inducer enabling external control of expression of the gene controlled by the receptor (See, for example, PCT/GB96/01195).

Accordingly, there is a need in the art for improved systems to precisely modulate the expression of exogenous genes in mammalian subjects. For example, a non-mammalian-based transcription regulating system would be extremely desirable for general application to transgene regulation in in vitro, ex vivo, and in vivo applications. In addition, there is a need in the art for new and better methods of using steroid/thyroid hormone nuclear receptors that require a dimer partner for functional transactivation of transgene expression for use in somatic gene therapy and for laboratory models thereof.

BRIEF DESCRIPTION OF THE INVENTION

In accordance with the present invention, there are provided chimeric proteins comprising at least two functional protein units, wherein each functional protein unit comprises the dimerization domain of a member of the steroid/thyroid hormone nuclear receptor superfamily, and an optional linker interposed therebetween, wherein the at least two protein units form a functional entity. When the chimeric protein contains two functional protein units, the chimeric protein forms a functional dimer (FD), for example a heterodimer or a homodimer. In one embodiment according to the present invention, each protein unit comprises a ligand binding domain and an optional hinge domain of a steroid/thyroid hormone nuclear receptor member, and an optional DNA binding domain. The functionality of the entity is independent of the order of the protein units in the chimeric protein. Polynucleotides encoding the invention chimeric protein and cells containing such polynucleotide(s) are also provided according to the present invention. In one embodiment according to the present invention, the invention polynucleotide encodes the invention chimeric protein as a fusion protein, with one or more linker(s) encoded as a polypeptide linker.

In accordance with another embodiment of the present invention, there are provided methods for modulating the expression of exogenous gene(s) in a subject organism containing DNA construct(s) encoding and expressing invention chimeric protein(s) and DNA construct(s) encoding and expressing exogenous gene(s) under the control of a response element. The invention method for modulating the expression of exogenous gene(s) in a subject organism comprises administering to the subject an effective amount of an exogenous ligand for at least one functional unit of the chimeric protein.

The present DNA binding studies indicate that many of the invention functional dimers (FDs) display DNA binding equivalent or superior to that of receptor complexes formed from and/or containing identical wild type members of the steroid/thyroid hormone nuclear receptor superfamily (i.e., the same two members from which the invention chimeric protein is derived). Transient transfection analysis reveals that distinct groups of FD constructs transactivate responsive promoters in a manner similar to wild-type complexes, while others lose the capacity to transactivate and function like constitutive repressors.

Competition experiments and supporting data reveal that FDs favor dimerization with dimer partners contained within a chimeric protein over interaction with other wild type dimer partners. These results demonstrate that certain of the invention chimeric protein FDs share properties of monomeric receptor complexes while others have novel characteristics unique to individual constructs.

To enhance the possibility of producing a functional entity upon expression, the invention chimeric proteins allow for any of the protein units to be positioned at the amino terminus of the chimeric protein. In addition, to enhance flexibility for proper folding and three-dimensional orientation of the protein units into a functional entity, an optional linker can be interposed between the protein units in the chimeric protein. A variety of different linkers can be used in the invention chimeric proteins, including chemical and polypeptide linkers, with the latter being preferred if the entity is expressed as a fusion protein. In a presently preferred embodiment, the linker is designed to allow for incremental elongation of the linker distance interposed between the two protein units.

BRIEF DESCRIPTION OF THE FIGURES

In the interests of brevity and consistency, the names of receptors and dimer partners have been abbreviated for use herein as follows: "E", "U", or "R" alone indicates a monomeric receptor protein or dimer partner (i.e., not contained in an invention chimeric protein) containing, respectively, at least the ligand binding domain of the Drosophila ecdysone receptor, the ultraspiracle protein, or the retinoid X receptor. When contained within an invention "fusion protein", which is alternatively referred to herein as a "functional dimer", these receptor proteins are represented by "E", "U", or "R" separated by either an "N", representing a linker of any length, or a numeral from 0 to 20, indicative of a linker containing a specific number of linker segments wherein each linker segment contains 12 amino acids. In the description of invention fusion proteins, which are functional dimers, the leading letter in the abbreviation indicates the receptor protein at the amino terminus of the fusion protein. For example, E5U means a fusion protein having at least the ligand binding domain, hinge domain, and optionally functional DNA binding domain of Drosophila ecdysone receptor at the amino terminus, a linker containing 5 linker segments (of 12 amino acids each, plus the 5 amino acid linker bridge (i.e., a linker containing a total of 65 amino acids) and the comparable domains of the ultraspiracle protein. An initial "V" in the construct abbreviation, e.g., VE5U or VE, indicates fusion of the VP16τ activation domain to the N-terminus of the fusion protein, as described more completely hereafter.

FIG. 1 is a schematic diagram of a nucleic acid construct encoding invention fusion proteins that contain EcR with a dimer partner, U (Usp) or R (RXR). "D"=DNA binding domain; "L"=ligand binding domain; curvilinear line=fusion bridge. "Individual" (SEQ ID NOS: 76 & 77 which encode SEQ ID NO: 79) represents a nucleotide sequence that encodes the wild type C terminus of EcR (receptor) and the monomeric N-terminus of RXR (binding partner) before introduction of a nucleotide sequence encoding a fusion bridge. "Fused" (SEQ ID NO: 78) represents the same segments with nucleotides inserted that encode a 5 amino acid fusion bridge (amino acids 3–7 of SEQ ID NO: 80) containing the SfiI insertion site. "Tether" (SEQ ID NOS: 30 & 31) indicates a nucleotide sequence that encodes a 12 amino acid linker (SEQ ID NO: 15) to be inserted into the SfiI site of the fusion bridge to produce fusion proteins with greater spacing between the two protein units (i.e., dimer partners) in the invention fusion protein.

FIG. 2A is a graph quantifying gel mobility shift as a result of response element binding to invention endodimer FDs in the presence of murA. Controls were treated either with vehicle (open bars, i.e., −MurA) or with 1 µM murA as ligand (black bars, i.e., +MurA). Bars are labeled along the bottom with FDs named as described in the text. E represents an EcR only control; NON represents a non-transfected control. E+U and E+R are control lanes of monomeric in vitro translated proteins used for sizing of endodimer band shifts. Numbers at the top of each bar represent relative-fold increase in response element binding resulting from ligand treatment.

FIG. 2B is a schematic representation of five F-domain deletion constructs containing EcR (darkly shaded) and RXR (lightly shaded) with no linker polypeptide (EOR). Incremental deletions are shown to NheI, PvuII, NarI, and BglII sites within the ecdysone receptor F domain. The top schematic represents E0R (1340 amino acids) containing the complete F-domain (bracketed); the second schematic represents a deletion (Δ60 amino acids) to the NheI site; the third schematic represents a deletion (Δ138 amino acids) to the PvuII site; the fourth schematic represents a deletion (Δ198 amino acids) to the NarI site; and the fifth schematic represents a deletion (Δ228 amino acids) to the BglII site.

FIG. 4A is a graph showing a comparison of luciferase activity in relative light units (RLU) in transient transfection assays conducted with or without ligand, using either monomeric receptors having amino terminal fused VP16 activation domains or invention FDs containing EcR, RXR, and a linker with a variable number of linker segments. Cells were treated with vehicle (open bars, i.e., −MurA), or 1 µM muristerone A as ligand (black bars, i.e., +MurA). Numbers at the top of the bars indicate the fold-increase relative to FD or monomeric receptor without addition of monomeric VRXR (VR) or monomeric VUsp (VU). E=EcR only; E4-luc=reporter plasmid only; and FIG. 4B is a graph showing a comparison of luciferase activity as in FIG. 4A herein, except that the FDs contain Usp in place of RXR.

FIG. 5 is a series of three graphs showing repression of ligand-stimulated luciferase expression by monomeric receptors caused by competition with the invention ENU and UNE FDs when transiently co-transfected into 293 cells and treated either with vehicle (open bars, i.e., −MurA), or 1 µM muristerone A as ligand (black bars, i.e., +MurA). Decimal numbers on the abscissa represent molar amount of FD relative to VE plasmid (1.0 is equimolar FD:VE).

FIG. 7A represents a native dimer; FIG. 7B represents a disorganized fusion protein; FIG. 7C represents an endodimer orientation of a single invention FD; FIG. 7D represents a tetramer of two invention FDs; FIG. 7E represents a multimer of four invention FDs.

DETAILED DESCRIPTION OF THE INVENTION

Figure 2A:
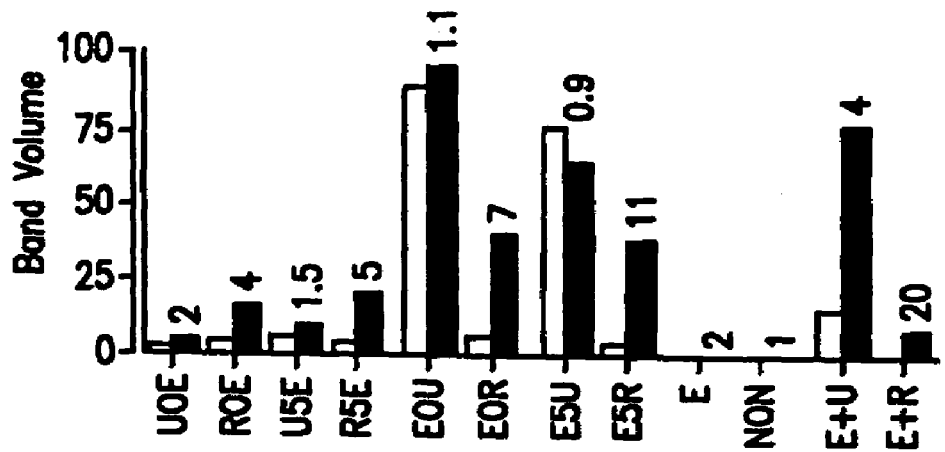
FIGS. 2A–B illustrate the results of gel mobility shift assays of response element binding of the invention FD constructs having linkers containing either 0 or 5 linker segments as compared with that of monomeric receptor complexes (translated in vitro).

In accordance with the present invention, there are provided chimeric proteins comprising at least two functional protein units, wherein each functional protein unit comprises the dimerization domain of a member of the steroid/thyroid hormone nuclear receptor superfamily, and an optional linker interposed therebetween, wherein the at least two protein units form a functional entity. When the chimeric protein contains two functional protein units, the chimeric protein forms a functional dimer (FD), for example a heterodimer or a homodimer.

The invention chimeric proteins form functional entities (e.g. functional dimers) under a variety of conditions. Such conditions include, but are not limited to, those at or near physiological conditions (e.g., in saline at body temperature). Those of skill in the art will understand that formation of invention functional entities by dimerization or crystallization of a macromolecule can be influenced by manipulation of a variety of physical parameters, such as are disclosed in McPherson, *Eur. J. Biochem.*, 189:1–23, 1990, which is incorporated herein by reference in its entirety. Due to the proximity of the protein units within the invention chimeric protein, dimerization tends to take place with intramolecular partners, rather than with other suitable monomeric dimer partners with which the protein units in the chimeric protein might otherwise interact.

As used herein, plural nouns and verbs are intended to signify the singular form as well as the plural form of the particular noun or verb, unless prefixed by an adjective indicating a specific number, such as "two feet" or "three ligands", and a singular noun or verb is intended to include the plural form, unless prefixed by a phrase clearly indicating that only the singular noun or verb is intended, as in the phrase "one and only one foot" or "only one ligand."

Each chimeric protein in the invention system is required to contain a dimerization domain of a member of the steroid/thyroid hormone nuclear receptor superfamily. As used herein, "dimerization domain" means a region of a member of the steroid/thyroid hormone nuclear receptor superfamily containing a sequence of amino acids that functions to cause dimerization of two members of the steroid/thyroid hormone nuclear receptor superfamily. Members of the steroid/thyroid hormone nuclear receptor superfamily are commonly characterized by the presence of five domains: N-terminal or activation domain (A/B), DNA binding domain (C), hinge domain (D), ligand binding domain (E), and C-terminal domain (F) (Evans, R. *Science* 240:889–895, 1988). The dimerization domain is generally located within the region of the receptor molecule that is referred to as including the D, E and F domains, or is referred to as the "D-E-F" domain. Typically the dimerization domain includes the complete ligand binding domain (E) and may optionally include all or part of the hinge domain (D) and/or the C-terminal region (F) of a member of the steroid/thyroid nuclear receptor superfamily, or a functional equivalent thereof. In some cases the dimerization domain may include at least a portion of the DNA binding domain itself. Multiple domains of a given receptor can act in concert as well as independently. Therefore, as employed herein, the term "dimerization domain of a member of the steroid/thyroid hormone nuclear receptor superfamily" refers to that portion (or portions) of a member of the steroid/thyroid hormone nuclear receptor superfamily that is involved in the formation of a dimer.

As used herein, the term "fusion protein" means a genetically engineered molecule in which two or more polypeptide units are fused into a single polypeptide molecule by fusion of the open reading frames (ORFs) encoding the two or more separate protein units into a single ORF. The invention fusion proteins are capable of forming a "functional entity" in the optional presence of ligand. When the fusion proteins contain two protein units, a "functional dimer (FD)" is formed by dimerization.

As used herein, the term "functional dimer" or "functional entity" as applied to an invention chimeric protein means that the functional entity or dimer possesses at least some of the biological function of a dimer formed between two equivalent monomeric (i.e. undimerized) polypeptide units, or between two equivalent monomeric members of the steroid/thyroid hormone nuclear receptor superfamily. The biological function of such dimers includes one or more of the following properties: DNA binding, ligand binding, transactivation, and dimerization properties related to transactivation of a promoter operatively associated with a response element responsive to the invention chimeric protein. For example, invention chimeric protein(s) can modulate transactivation of gene(s) whose expression is controlled by the presence of ligand (e.g. an invention FD wherein at least one member is a *Bombyx mori* ecdysone receptor can modulate the expression of a gene under the control of a *Bombyx* ecdysone response element).

Therefore, the term "functional protein units" as applied to the functional entity or dimer formed by an invention chimeric protein means that the at least two protein units in the functional entity or dimer possess a cooperative function. For example, in a functional dimer the two dimerization domains (e.g., the two protein units) fold and interact with each other in a manner appropriate to substantially preserve one or more of the above named biological functions in the functional dimer that are present when corresponding monomeric members of the dimer come together under physiological conditions to form a native dimer complex.

Figure 7A:
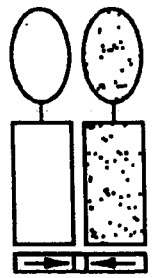
FIGS. 7A–E are a series of six schematic diagrams representing possible conformations of receptor FDs described in the text. Stippled and white oval/rectangles represent receptors, small rectangles with interior arrows represent EcREs, and curvilinear lines represent linkers between protein units in the invention fusion proteins.
Figure 7B:
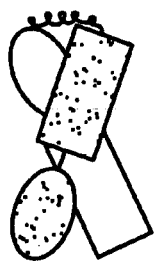
Figure 7C:
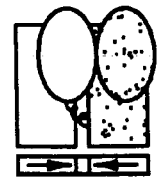
Figure 7D:
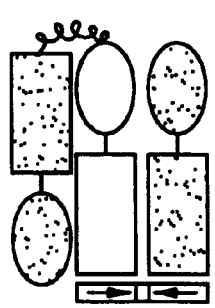
Figure 7E:
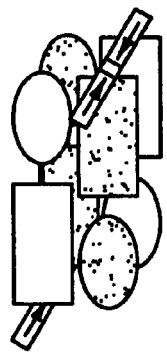
Figure 7F:
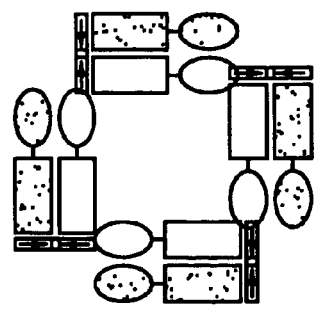
Figure 8:
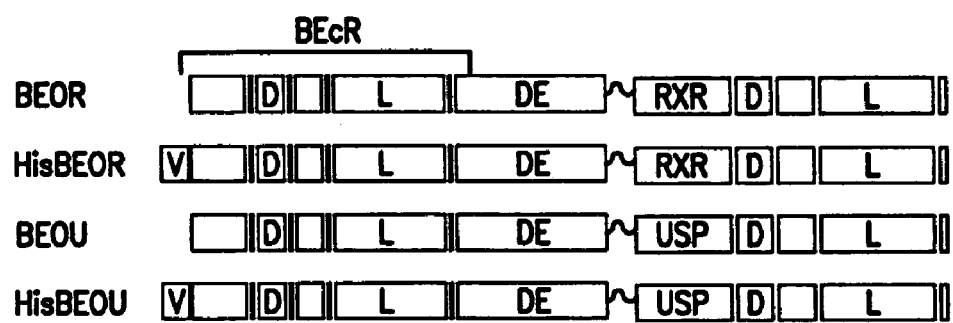
FIG. 8 is a series of schematic representations of invention FDs containing *Bombyx* ecdysone receptor (BEcR) plus the entire F domain of the *Drosophila melanogaster* ecdysone receptor (amino acids 650 to 878) (DE), which segment is included for ease in making the construct (DEcR). The BEcR is at the amino terminus of the fusion protein with either RXR or Usp as the dimer partner at the carboxy terminus of the fusion protein. "D"=DNA binding domain; "L"=ligand binding domain; curvilinear line=fusion bridge. "H"=an N-terminal His tag for protein purification.

As used herein the term "endodimer" means a dimer formed in an orientation approximating that of a native dimer complex formed between equivalent monomeric polypeptides, i.e., an "internal" dimer. FIG. 7A illustrates a native dimer complex and FIG. 7C illustrates an invention endodimer.

As used herein the term "dimer partner" means any polypeptide that, under physiological conditions, forms a dimer with a member of the steroid/thyroid hormone nuclear receptor superfamily. Such dimer partners include, but are not limited to, monomeric member(s) of the steroid/thyroid hormone nuclear receptor superfamily, including those known in the art as a "silent partner," which are characterized by forming dimeric species with a member of the steroid/thyroid superfamily of receptors wherein the silent partner may not directly participate in binding ligand (i.e., only the co-partner in the fusion protein binds ligand). Exemplary dimer partner(s) include RXR, Usp, Nurr1, and the like.

The term "dimer partner" is meant to include members of the steroid/thyroid hormone nuclear receptor superfamily to which other wild type members preferentially bind to form heterodimeric species. For example, wild type members of the steroid/thyroid hormone nuclear receptor superfamily preferentially form heterodimers with a common partner, the retinoid X (or 9-cis retinoic acid) receptor (RXR, see, for example, Yu et al., *Cell*, 67:1251–1266, 1991; Bugge et al., *EMBO J.*, 11:1409–1418, 1992; Kliewer et al., *Nature* 355:446–449, 1992; Leid et al., *Cell* 68:377–395, 1992; Marks et al., *EMBO J.* 111:1419–1435, 1992; Zhang et al., *Nature* 3:441–446, 1992; Issemann et al., *Biochimie*, 75:251–256, 1993). Additional dimer partners for members of the steroid/thyroid hormone nuclear receptor superfamily include ultraspiracle (Usp), farnesoid X receptor (FXR), and the like.

As used herein, the phrase "member(s) of the steroid/thyroid hormone nuclear receptor superfamily" (also known as "intracellular receptors" or "the nuclear receptor superfamily") refers to hormone binding proteins that operate as ligand-dependent transcription factors, including identified members of the steroid/thyroid hormone nuclear receptor superfamily for which specific ligands have not yet been identified (referred to in the art as "orphan receptors").

Exemplary members of the steroid/thyroid hormone superfamily of receptors (including the various isoforms thereof) include steroid receptors such as glucocorticoid receptor (GR), mineralocorticoid receptor (MR), estrogen receptor (ER), progesterone receptor (PR), androgen receptor (AR), vitamin $D_3$ receptor (VDR), and the like; plus retinoid receptors, such as the various isoforms of retinoic acid receptor (e.g., RARα, RARβ or RARγ), the various isoforms of retinoid X (or 9-cis retinoic acid) receptor (e.g., RXRα, RXRβ, or RXRγ), various isoforms of peroxisome proliferator-activated receptors (e.g., PPARα, PPARγ, PPARδ) and the like (see, e.g., U.S. Pat. Nos. 4,981,784;

5,171,671; and 5,071,773); thyroid hormone receptor (T₃R), such as TRα, TRβ, and the like; steroid and xenobiotic receptor (SXR, see for example, Blumberg et al., *Genes Dev* (1998) 12(20):3195–205), RXR-interacting proteins (RIPs; see, e.g., Seol et al., *Mol Endocrinol* (1995) 9(1):72–85; Zavacki et al., *Proc Natl Acad Sci USA* (1997) 94(15): 7909–14) including farnesoid X receptor (FXR; see for example, Forman et al., *Cell* (1995) 81(5):687–93; Hanley et al., *J Clin Invest* (1997) 100(3):705–12, O'Brien et al., *Carcinogenesis* (1996) 17(2):185–90), pregnenolone X receptor (PXR; see for example, Schuetz et al., *Mol Pharmacol* (1998) 54(6):1113–7), liver X receptor (LXR, see, e.g., Peet et al., *Curr Opin Genet Dev* (1998) 8(5):571–5), BXR (Blumberg et al., Genes Dev (1998) 12(9):1269–77), insect derived receptors such as the ecdysone receptor (EcR), the ultraspiracle receptor (see, for example, Oro et al., in *Nature* 347:298–301 (1990)), and the like; as well as other gene products which, by their structure and properties, are considered to be members of the superfamily, as defined hereinabove, including the various isoforms thereof (see, e.g., Laudet, V., *J Mol Endocrinol* (1997) 19(3):207–26).

Examples of orphan receptors contemplated for use herein include HNF4 (see, for example, Sladek et al., *Genes &Development* 4:2353–2365 (1990)), the COUP family of receptors (see, for example, Miyajima et al., in *Nucleic Acids Research* 16:11057–11074 (1988), and Wang et al., *Nature* 340:163–166 (1989)), COUP-like receptors and COUP homologs, such as those described by Mlodzik et al., *Cell* 60:211–224 (1990) and Ladias et al., *Science* 251:561–565 (1991), orphan receptor (OR1; see, e.g., Feltkamp et al., *J Biol Chem* (1999) 274(15):10421–9), the insect derived knirps and knirps-related receptors, short heterodimer partner (SHP; see, e.g., Seol et al., *Mol Cell Biol* (1997) 17(12):7126–31), hepatocyte nuclear receptor 4 (HNF4), constitutive androstane receptor (CAR; see, e.g., Forman et al., *Nature* (1998) 395(6702):612–5), and the like.

Each protein unit in the invention chimeric protein is required to contain at least a dimerization domain, optionally, the entire ligand binding domain, an optional hinge domain, and an optionally functional DNA binding domain of a member of the steroid/thyroid nuclear receptor superfamily, or a functional equivalent thereof. For use in the invention methods for modulating the transcription of exogenous or endogenous nucleic acids in a host, the ligand binding domains are either endogenous or non-endogenous to a host, with the latter including ligand binding domains that are modified to be non-responsive to ligands endogenous or native to the host. In embodiments wherein the ligand binding domain is derived from non-mammalian member(s) of the steroid/thyroid hormone nuclear receptor superfamily, which members are not normally present in the cells of a host, the ligand binding domains are preferably derived from the carboxy-terminal portion of non-mammalian members. Exemplary members that are not normally present in mammalian cells include insect, avian, amphibian, reptilian, fish, plant, bacteria, viral and fungal (including yeast) members of the steroid/thyroid hormone nuclear receptor superfamily, and the like.

Exemplary ligand binding domains derived from insect receptors include those derived from lepidopteran species such as *Drosophila melanogaster* (M. R. Koelle, 1995), *Bombyx mori* (Swevers et al., *Insect Biochem. Molec. Biol.*, 25(7):857–866, 1995), *Choristoneura fumiferana* (Palli et al., *Insect Biochem. Molec. Biol*, 26(5):485–499, 1996), *Manduca sexta* (Fujiwara et al., *Insect Biochem. Molec. Biol.*, 25(7):845–856, 1995), *Aedes aegypti* (Cho et al., *Insect Biochem Molec. Biol.*, 25: 19–27, 1995), *Chorinomus tentans* (Imhof et al., *Insect Biochem. Molec. Biol.*, 25:115–124, 1993), and the like.

When the functional protein units included in the invention chimeric protein lack a substantial portion of the C-terminal "F" domain in the dimerization domain of a native member of the steroid/thyroid hormone nuclear receptor superfamily, a functional protein unit that is less than about 700 amino acids in length is provided.

Ligand binding domains can be functionally located in either orientation and at various positions within the protein unit. For example, the ligand binding domain can be positioned at either the amino or carboxy terminus of the protein unit in the invention chimeric protein, or therebetween. In a preferred embodiment of the present invention, the ligand binding domain is positioned at the carboxy terminus of the protein unit (see FIG. 1).

The optional hinge region, when present, can also be functionally located in either orientation and at various positions within the protein unit. For example, the hinge region can be positioned at either the amino or carboxy terminus of the protein unit, or therebetween. Preferably, the hinge region is positioned internally between the ligand binding and DNA binding domains of one or more of the members in the chimeric protein. The hinge region bounded by the ligand binding domain and DNA binding domain of the native *Bombyx mori* receptor (BEcR), specifically, about 27 amino acid residues (i.e. amino acid residues 283–309, in the hinge region of BEcR) are sufficient to confer high affinity for complex formation with an endogenous dimer partner (see U.S. patent application Ser. No. 08/891,298, filed Jul. 10, 1997, copending herewith).

Each protein unit in the invention chimeric protein also optionally contains a DNA binding-domain. DNA-binding domains contemplated for use in the preparation of invention chimeric proteins are well known in the art and are typically obtained from DNA-binding proteins (e.g., transcription factors). The term "DNA-binding domain" is understood in the art to refer to an amino acid sequence that is able to bind to DNA. As used herein, the term "DNA-binding domain" encompasses a minimal peptide sequence of a DNA-binding protein up to the entire length of a DNA-binding protein, so long as the DNA-binding domain functions to associate with a particular regulatory element.

DNA-binding domains are known to function heterologously in combination with other functional domains by maintaining the ability to bind the natural DNA recognition sequence (see, e.g., Brent and Ptashne, *Cell*, 43:729–736, 1985). For example, with respect to steroid/thyroid hormone nuclear receptors, DNA-binding domains are interchangeable, thereby providing numerous chimeric receptor proteins (see, e.g., U.S. Pat. No. 4,981,784; and R. Evans, *Science*, 240:889–895, 1988). Similar to the ligand binding domain, the DNA-binding domain can be positioned at either the carboxy terminus or the amino terminus of a protein unit in the invention chimeric protein, or the DNA-binding domain can be positioned between the ligand binding domain and the activation domain. In preferred embodiments of the present invention, the DNA-binding domain is positioned internally between the ligand binding domain and the activation domain.

"DNA-binding protein(s)" contemplated for use herein belong to the well-known class of proteins that are able to directly bind DNA and facilitate initiation or repression of transcription. Exemplary DNA-binding proteins contemplated for use herein include transcription control proteins (e.g., transcription factors and the like; see, for example, Conaway and Conaway, *Transcription Mechanisms and*

*Regulation,* Raven Press Series on Molecular and Cellular Biology, Vol. 3, Raven Press, Ltd., New York, N.Y., 1994).

Transcription factors contemplated for use herein as a source of such DNA binding domains include, e.g., homeobox proteins, zinc finger proteins, hormone receptors, helix-turn-helix proteins, helix-loop-helix proteins, basic-Zip proteins (bZip), β-ribbon factors, and the like. See, for example, S. Harrison, "A Structural Taxonomy of DNA-binding Domains," *Nature,* 3:715–719. Homeobox DNA-binding proteins suitable for use herein include, for example, HOX, STF-1 (Leonard et al., *Mol. Endo.,* 7:1275–1283, 1993), Antp, Mat α-2, INV, and the like. See, also, Scott et al. *Biochem. Biophys. Acta,* 989:25–48, 1989. It has been found that a fragment of 76 amino acids (corresponding to amino acids 140–215 described in Leonard et al., 1993) containing the STF-1 homeodomain binds DNA as tightly as wild-type STF-1. Suitable zinc finger DNA-binding proteins for use herein include Zif268, GLI, XFin, and the like. See also, Klug and Rhodes, *Trends Biochem. Sci.,* 12:464, 1987; Jacobs and Michaels, *New Biol.,* 2:583, 1990; and Jacobs, *EMBO J,* 11:4507–4517, 1992.

An additional DNA binding domain contemplated for use in the practice of the present invention is the GAL4 DNA binding domain. The DNA binding domain of the yeast GAL4 protein comprises at least the first 74 amino terminal amino acids thereof (see, for example, Keegan et al., *Science* 231:699–704, 1986). Preferably, the first 90 or more amino terminal amino acids of the GAL4 protein will be used, for example, the 147 amino terminal amino acid residues of yeast GAL4.

The DNA-binding domain(s) used in the invention chimeric proteins can be obtained from a member of the steroid/thyroid hormone nuclear receptor superfamily, or are substantially the same as those obtained from a member of the superfamily. The DNA-binding domains of all members of the steroid/thyroid hormone nuclear receptor superfamily are related. Such domains consist of 66–68 amino acid residues, and possess about 20 invariant amino acid residues, including nine cysteines. Members of the superfamily are characterized as proteins which contain these 20 invariant amino acid residues. The highly conserved amino acids of the DNA-binding domain of members of the superfamily are as follows:

Cys-X-X-Cys-X-X-Asp*-X-Ala*-X-Gly*-
X-Tyr*-X-X-X-X-Cys-X-X-Cys-Lys*-X-
Phe-Phe-X-Arg*-X-X-X-X-X-(X-X-)Cys-
X-X-X-X-X-(X-X-X-)Cys-X-X-X-Lys-X-
X-Arg-X-X-Cys-X-X-Cys-Arg*-X-X-
Lys*-Cys-X-X-X-Gly*-Met(SEQ ID NO:1);

wherein X designates non-conserved amino acids within the DNA-binding domain; an asterisk denotes the amino acid residues which are almost universally conserved, but for which variations have been found in some identified hormone receptors; and the residues enclosed in parenthesis are optional residues (thus, the DNA-binding domain is a minimum of 66 amino acids in length, but can contain several additional residues).

Invention chimeric proteins are optionally modified by the introduction of an activation domain subunit. Activation domains contemplated for use in the practice of the present invention are well known in the art and can readily be identified by those of skill in the art. Such activation domains are typically derived from transcription factors and comprise a contiguous sequence that functions to activate gene expression when associated with a suitable DNA-binding domain and a suitable ligand binding domain. An activation domain can be positioned at any convenient site within the invention chimeric protein, e.g., at the carboxy terminus, the amino terminus, or between the ligand binding domain and the DNA binding domain within one or both protein units of the chimeric protein. In presently preferred embodiments of the invention, the activation domain is positioned at the amino terminus of the invention chimeric protein.

Suitable activation domains can be obtained from a variety of sources, e.g., from the N-terminal region of members of the steroid/thyroid hormone nuclear receptor superfamily, from transcription factor activation domains, such as, for example, VP16, GAL4, NF-kB or BP64 activation domains, and the like. The activation domain presently preferred for use in the practice of the present invention is obtained from the C-terminal region of the VP 16 protein, and is known as VP16τ.

In a presently preferred embodiment of the present invention, chimeric proteins contain one or more ecdysone receptors (EcR) as the steroid/thyroid hormone nuclear receptor, for example, a *Drosophila* EcR (DEcR) or a *Bombyx* EcR (BEcR). The chimeric protein further comprises either RXR or ultraspiracle protein (Usp) as an additional functional protein unit. The preferred order within the chimeric protein is for the EcR to be located at the amino terminus of the chimeric protein. However, when the invention chimeric protein further comprises an activation domain, the activation domain is preferably located at the amino terminus of the chimeric protein.

The EcR, an insect receptor, differs in two respects from other known steroid/thyroid hormone nuclear receptor superfamily. First, EcR has very different documented relationships with two similar dimer partners: its natural partner, Usp, and the mammalian homolog, RXR. EcR also differs from other members of the steroid/thyroid hormone nuclear receptor superfamily in that its apparent affinity to these heterodimer partners varies depending on the presence of ligand.

To facilitate dimerization of the dimerization domains in the invention chimeric proteins, the at least two protein units of the chimeric protein preferably have the ligand binding domain, hinge domain, and DNA binding domain in the same order within each protein unit. If the chimeric protein additionally contains an activation domain, the activation domain is preferably located at the amino terminus of the chimeric protein, ahead of the first unit thereof, as illustrated in Examples 1 and 4 herein.

Invention chimeric protein(s) optionally further contain a linker interposed between one or more of the protein units. The protein units can be independently oriented amino terminus to carboxy terminus within the chimeric protein, or visa versa. For example, the linker can be placed between the carboxy terminus of the first protein unit and the amino terminus of the second protein unit. Any type of linker known in the art can be used for linking the protein units in invention chimeric proteins so long as the linker is flexible and does not interfere with dimerization between protein units in the invention chimeric proteins.

In one embodiment according to the present invention, the linker is a heterobifunctional cleavable cross-linker, such as N-succinimidyl (4-iodoacetyl)-aminobenzoate; sulfosuccinimidyl(4-iodoacetyl)-aminobenzoate; 4-succinimidyl-oxycarbonyl-α-(2-pyridyldithio) toluene; sulfosuccinimidyl-6-[α-methyl-α-(pyridyldithiol)-toluamido]hexanoate; N-succinimidyl-3-(-2-pyridyldithio)-proprionate; succinimidyl-6-[3(-(-2-pyridyldithio)-proprionamido]hexanoate; sulfosuccinimidyl-6-[3(-(-2-pyridyldithio)-propionamido]hexanoate; 3-(2-pyridyldithio)-propionyl hydrazide, Ellman's reagent, dichlorotriazinic acid, S-(2-thiopyridyl)-L-cysteine, and the like. Further bifunctional linking compounds are disclosed in U.S. Pat. Nos. 5,349,066, 5,618,528, 4,569,789, 4,952,394, and 5,137,877, each of which is incorporated herein by reference in its entirety. These chemical linkers can be attached to purified proteins using numerous protocols known in the art, such as those described in Pierce Chemicals "Solutions, Cross-linking of Proteins: Basic Concepts and Strategies," Seminar #12, Rockford, Ill.

In another embodiment according to the present invention, the linker can be a peptide having from about 2 to about 60 amino acid residues, for example from about 5 to about 40, or from about 10 to about 30 amino acid residues, such as is known in single-chain antibody research. Examples of such known linker moieties include GGGGS (SEQ ID NO:2), (GGGGS)$_n$ wherein n=2 to 12; SEQ ID NO:3 refers to the preceding sequence wherein n=2; SEQ ID NOS:66–75 refer, respectively, to the preceding sequence wherein n=3 to 12, GKSSGSGSESKS (SEQ ID NO:4), GSTSGSGKS-SEGKG (SEQ ID NO:5), GSTSGSGKSSEGSGSTKG (SEQ ID NO:6), GSTSGSGKSSEGKG (SEQ ID NO:7), GSTSGSGKPGSGEGSTKG (SEQ ID NO:8), EGKSSGSGSESKEF (SEQ ID NO:9), SRSSG (SEQ ID NO:10), SGSSC (SEQ ID NO:11), and the like. A *Diphtheria* toxin trypsin sensitive linker having the sequence AMGRSGGGCAGNRVGSSLSCGGLNLQAM (SEQ ID NO:12) is also useful. Alternatively, the peptide linker moiety can be VM or AM, or have the structure described by the formula: AM(G$_{2\ to\ 4}$S)$_x$AM wherein x is an integer from 1 to 11, wherein SEQ ID NO:13 refers to the formula AM(G$_2$S)$_1$AM; SEQ ID NOS:34–43 refer to the formula AM(G$_2$S)$_{2\ to\ 11}$AM, respectively; SEQ ID NOS:44–54 refer to the formula AM(G$_3$S)$_{1\ to\ 11}$AM, respectively; and SEQ ID NOS:55–65 refer to the formula AM(G$_4$S)$_{1\ to\ 11}$AM, respectively. Additional linking moieties are described, for example, in Huston et al., *PNAS* 85:5879–5883, 1988; Whitlow, M., et al., *Protein Engineering* 6:989–995, 1993; Newton et al., *Biochemistry* 35:545–553, 1996; A. J. Cumber et al., *Bioconj. Chem.* 3:397–401, 1992; Ladurner et al., *J. Mol. Biol.* 273:330–337, 1997; and U.S. Pat. No. 4,894,443, the latter of which is incorporated herein by reference in its entirety.

Generally, however, the linker contains from about 5 to about 245 amino acids, although there is no theoretical upper limit on the number of amino acids that could be used in the linker. Preferably, the linker contains from about 53 to about 125 amino acids. The amino acids in the linker protein are preferably selected to provide flexibility to the linker. Preferably, a multiplicity of flexibility enhancing amino acids, such as proline, glycine, alanine and serine, are incorporated into the linker to enhance its flexibility.

Assuming a span of approximately 3.35 angstroms per amino acid within the flexible peptide bridge encoded by a 36-base pair SfiI compatible oligonucleotide, the predicted minimum and maximum distance for the lengths of the linker having from 0 to 20 linker segments ranges from about 16.75 angstroms (the 5 amino acid bridge) to 804 angstroms (20-linker segments+the 5 amino acid bridge). Thus, the length of the linker can readily be selected to enhance dimerization between any two particular members acting as dimer partners by including as many linker segments as is preferred to enhance the biological functions of the functional dimer, as discussed herein.

In a presently preferred embodiment, the nucleotide encoding the polypeptide linker contains a restriction endonuclease recognition site which produces an overhang composed of non-palindromic center bases to allow for insertion of compatible inserts in a uniform orientation and in continually in-frame blocks along the length of the polypeptide linker. This type of linker allows incremental expansion of the linker peptide to produce chimeric proteins containing linkers with a range of distances between the protein units. The nucleotide encoding the linker preferably contains a rare 8-base-pair SfiI recognition site that is useful in making constructs with linkers of variable length. In addition, the nucleotides composing the recognition site:

-GGCCNNNNNGGCC- (SEQ ID NO:14)

are guanidines and cytosines, which can be oriented in frame to encode glycine and proline residues in accordance with the criteria of producing a "flexible" protein linker for junction of the two units of the chimeric protein. Any bases can be used as the "N" nucleotides contained within the recognition site, allowing further flexibility in the design of the linker.

A presently preferred linker amino acid sequence is GPGGGSGGGSGT (SEQ ID NO:15), which provides a high degree of predicted flexibility while minimizing repetitive sequence within the encoding oligonucleotide.

In accordance with another embodiment of the present invention, there are provided nucleotides encoding invention chimeric protein(s) and cells containing such nucleotides. Cells containing invention polynucleotides can be either mammalian or non-mammalian, for example, plant or fingi cells, and the like.

In accordance with another embodiment of the present invention, there are provided methods for modulating the expression of exogenous gene(s) in a subject organism containing:

1) a functional entity according to the invention and
2) a DNA construct encoding and expressing the exogenous gene(s) under the control of a response element responsive to the functional dimer.

Invention methods for modulating exogenous gene expression in such a subject organism comprise administering to the subject organism an effective amount of at least one ligand for the functional dimer.

Ligand is selected to activate at least one functional unit of the functional entity. When the functional entity is a functional dimer, the ligand is usually selected to activate the dominant member of the functional dimer. For example, if one of the two members in the functional dimer is a silent dimer partner, the ligand is selected to activate the member in the functional dimer that does not act as a silent dimer partner.

In a presently preferred embodiment of the present invention, one of the members in the functional entity is from an insect species, and the preferred ligand is an insect hormone. For example, preferred insect receptors are the *Drosophila* ecdysone receptor or the *Bombyx* ecdysone receptor, and the preferred dimer partner with these insect receptors in the invention chimeric protein is either the ultraspiracle protein or a retinoid X receptor. These functional entities complex with the ecdysone response element, generally in the presence of ligand for the functional dimer formed by the invention chimeric protein, but in some instances the presence of ligand is not required to form a functional entity/response element complex, as explained more fully hereinbelow.

As employed herein, the terms "modulate" and "modulating" refer to the ability of a given functional entity to activate/deactivate and/or up-regulate/down-regulate transcription of exogenous nucleic acids, relative to the transactivation activity in the absence of the functional entity.

The actual effect of an invention functional entity on the transcription of exogenous or endogenous nucleic acids will vary depending on the particular combination of dimerization domains and/or members of the steroid/thyroid hormone nuclear receptor superfamily in the chimeric protein, on the presence or absence of specific ligand for the ligand binding domain(s) employed in the chimeric protein, and on the regulatory element (e.g., response element) with which the selected chimeric protein interacts. It is specifically contemplated within the scope of the present invention that modulation includes repression of expression of one or more genes. Such repression can be either ligand-dependent repression or repression that occurs independently of the presence of a ligand. Thus, there are four types of modulation contemplated within the scope of the invention: ligand-dependent induced modulation, ligand-dependent repressed modulation, ligand-independent induced modulation, and ligand independent repressed modulation. The ligand can be either exogenous or endogenous to the subject treated for modulation of expression of an exogenous gene.

More particularly, the type of modulation that results from the practice of the invention method (i.e., whether activation or repression of expression of the exogenous gene) depends upon the combination of dimerization domains and/or members of the steroid/thyroid hormone nuclear receptor superfamily contained within a functional entity formed by the invention chimeric protein. For example, it has been determined that activation of expression of the exogenous gene(s) according to the invention modulation method can be achieved if the dimer partners in an invention FD used in the invention method of modulation are an ecdysone receptor and a retinoid X receptor, e.g. EOR or E5R. Ligands suitable for activating expression of the exogenous gene(s) when such functional dimers are employed in the invention methods include muristerone A, 20-hydroxyecdysone, phytoecdysteroid(s), and the like.

On the other hand, it has been determined that expression of an exogenous gene(s) can be repressed independently of (i.e., with or without) the presence of ligand if an invention FD comprising an ecdysone receptor (e.g., either a *Drosophila* ecdysone receptor or a *Bombyx* ecdysone receptor) and an ultraspiracle protein as dimer partner is used in the invention method, e.g., E5U, and the like. Ligands suitable for activating expression of the exogenous gene(s) when such functional dimers are employed in the invention methods are 20-hydroxyecdysone, muristerone A, phytoecdysteroid(s), and the like. In addition, expression of exogenous gene(s) can be repressed independently of (i.e., with or without) the presence of ligand if an invention FD comprising a *Bombyx* ecdysone receptor and an RXR as dimer partner is used in the invention method. As shown in Example 6 herein, an N-terminal His tag on the chimeric protein to aid in protein purification does not effect binding of the chimeric protein to a suitable response element so as to repress expression of the exogenous gene according to invention methods for modulating expression of exogenous gene(s).

Accordingly, in another embodiment of the present invention, there are provided methods for modulating (i.e., either activating or repressing) the expression of one or more genes in a subject organism independently of the presence of ligand for the invention chimeric protein. If the subject organism contains an invention chimeric protein, the invention method comprises introducing to the subject an exogenous response element(s) with which the chimeric protein interacts and which controls expression of the one or more genes, thereby modulating expression of the gene(s) independent of the presence of ligand for the chimeric protein. On the other hand, if the subject organism contains an exogenous response element(s) controlling expression of the one or more genes, the invention method comprises introducing to the subject an invention chimeric protein with which the response element interacts, thereby modulating expression of the gene(s) independent of the presence of ligand for the chimeric protein.

In accordance with another embodiment of the present invention, there are provided methods for modulating (i.e., either activating or repressing) the expression of one or more exogenous genes independent of ligand for the chimeric protein. If the subject contains a chimeric protein according to the invention, the invention method comprises introducing to the subject an effective amount of a response element, wherein the response element is responsive to the chimeric protein and wherein the modulation is independent of ligand for the chimeric protein. The modulation can be ligand independent activation or ligand independent repression.

In accordance with another embodiment of the present invention, there are provided methods for modulating (i.e., either activating or repressing) the expression of one or more exogenous genes in a cell containing:
1) an invention chimeric protein and
2) a DNA construct comprising the exogenous gene under the control of a response element with which the chimeric protein interacts, wherein said response element controls expression of the exogenous gene, said method comprising administering to the cell an effective amount of an exogenous ligand for at least one functional unit of the chimeric protein.

In accordance with another embodiment of the present invention, there are provided methods for modulating the expression of one or more genes in a subject organism containing an endogenous response element controlling expression of one or more genes. The invention method in this situation comprises introducing to the subject an invention chimeric protein, wherein the chimeric protein interacts with the response element, thereby modulating expression of the gene(s) dependent on the presence of endogenous ligand therefor. The chimeric protein is encoded by an inducible DNA construct and the modulating comprises inducing expression of the gene(s).

In another embodiment according to the present invention, there are provided methods for modulating the expression of one or more genes in a subject organism containing an endogenous response element controlling expression of one or more genes and an endogenous ligand. The invention method comprises introducing to the subject an invention chimeric protein that interacts with the endogenous ligand and wherein the chimeric protein interacts with the response element, thereby modulating expression of the gene(s) dependent on the presence of the endogenous ligand. If the invention chimeric protein is encoded by an inducible DNA construct, the modulating further comprises inducing expression of the chimeric protein. This embodiment of the invention is especially useful for controlling expression of an exogenous gene that is under the control of an endogenous response element wherein the ligand for the invention functional dimer is also endogenous.

Response elements contemplated for use in the practice of the present invention (relating to modulation of the expression of exogenous genes in a subject) include native, as well as modified response elements. For example, since invention functional dimers can function as either homodimers or as heterodimers (with a silent partner therefor), any response element that is responsive to an invention functional dimer, in the form of a homodimer or heterodimer, is contemplated for use in the invention methods described herein. As is readily recognized by those of skill in the art, invention functional dimers (whether in the form of a homodimer or a heterodimer) can bind to a response element having an inverted repeat motif (i.e., two or more half sites in mirror image orientation with respect to one another), to a response element having a direct repeat motif, and the like.

Response elements useful in conjunction with invention functional entities are those well known in the art. As readily recognized by those of skill in the art, the response element employed will vary as a function of the protein units incorporated into the functional entity. Thus, for example, retinoic acid receptor response elements are composed of at least one direct repeat of two or more defined half sites separated by a spacer of five nucleotides. The spacer nucleotides can independently be selected from any one of A, C, G or T. Each half site of response elements contemplated for use in the practice of the invention comprises the sequence:

-RGBNNM-, wherein

R is selected from A or G;

B is selected from G, C, or T;

each N is independently selected from A, T, C, or G; and

M is selected from A or C;

with the proviso that at least 4 nucleotides of said -RGBNNM-sequence are identical with the nucleotides at corresponding positions of the sequence -AGGTCA-. Response elements employed in the practice of the present invention can optionally be preceded by $N_x$, wherein x falls in the range of 0 up to 5.

For example, thyroid hormone receptor response elements can be composed of the same half site repeats, with a spacer of four nucleotides. Alternatively, palindromic constructs as have been described in the art are also functional as TR response elements.

Exemplary GAL4 response elements are those containing the palindromic 17-mer:

5'-CGGAGGACTGTCCTCCG-3' (SEQ ID NO:16), such as, for example, 17MX, as described by Webster et al., in Cell 52:169–178 (1988), as well as derivatives thereof. Additional examples of suitable response elements include those described by Hollenberg and Evans in Cell 55:899–906 (1988); or Webster et al. in Cell 54:199–207 (1988).

Ecdysone response element sequences are preferred for use herein with functional dimers containing an ecdysone receptor function in a position- and orientation-independent fashion. The native ecdysone response element has been previously described, see, e.g., Yao et al., Cell, 71:63–72, 1992.

In the invention methods the operative response element is functionally linked to an operative exogenous gene(s) whose expression it is desirable to control. The word "operative" means that the respective DNA sequences (represented by the terms "response element" and "exogenous or endogenous gene") are operational, i.e., work for their intended purposes; the word "functionally" means that after the two segments are linked, upon appropriate activation by a functional dimer/ligand complex, the exogenous gene(s) will be expressed as the result of the fact that the "response element" was "turned on" or otherwise activated.

Certain nucleic acid constructs contemplated for use in one aspect of the present invention include promoters and regulatory elements operatively associated with exogenous nucleic acids. In one embodiment of the present invention, the invention functional dimer, in the presence of a ligand therefor, binds the regulatory element and activates transcription of one or more exogenous nucleic acids. For example, an invention functional dimer containing the protein units RXR and EcR will transactivate an ecdysone response element-containing promoter in the presence of the hormone ecdysone, or the synthetic analog, muristerone A.

Regulatory elements contemplated for use in the practice of the present invention include elements responsive to the invention receptor peptide. In a preferred embodiment of the present invention, such elements are exogenous regulatory elements not normally present in the cells of the host. One class of exogenous regulatory elements contemplated for use herein includes hormone response elements that modulate transcription of exogenous nucleic acid when bound to the DNA binding domain of an invention receptor peptide.

Regulatory elements employed in the practice of the present invention are operably linked to a suitable promoter for transcription of exogenous nucleic acid(s) product(s). As used herein, the term "promoter" refers to a specific nucleotide sequence recognized by RNA polymerase, the enzyme that initiates RNA synthesis. The promoter sequence is the site at which transcription can be specifically initiated under proper conditions. When exogenous nucleic acid(s), operatively linked to a suitable promoter, is(are) introduced into the cells of a suitable host, expression of the exogenous nucleic acid(s) is(are) controlled in many, but not all cases, by the presence of ligands, which are not normally present in the host cells.

Promoters contemplated for control of expression of exogenous nucleic acids employed in the practice of the present invention include inducible (e.g., minimal CMV promoter, minimal TK promoter, modified MMLV LTR), constitutive (e.g., chicken β-actin promoter, MMLV LTR (non-modified), DHFR), and/or tissue specific promoters.

Inducible promoters contemplated for use in the practice of the present invention comprise transcription regulatory regions that function maximally to promote transcription of mRNA under inducing conditions. Examples of suitable inducible promoters include DNA sequences corresponding to: the E. coli lac operator responsive to IPTG (see Nakamura et al., Cell, 18:1109–1117, 1979); the metallothionein promoter metal-regulatory-elements responsive to heavy-metal (e.g., zinc) induction (see Evans et al., U.S. Pat. No. 4,870,009), the phage T7lac promoter responsive to IPTG (see Studier et al., Meth. Enzymol, 185: 60–89, 1990; and U.S. Pat. No. 4,952,496), the heat-shock promoter; the TK minimal promoter; the CMV minimal promoter; a synthetic promoter; and the like.

Exemplary constitutive promoters contemplated for use in the practice of the present invention include the CMV promoter, the SV40 promoter, the DHFR promoter, the mouse mammary tumor virus (MMTV) steroid-inducible promoter, Moloney murine leukemia virus (MMLV) promoter, elongation factor 1a (EF1a) promoter, albumin promoter, APO A1 promoter, cyclic AMP dependent kinase II (CaMKII) promoter, keratin promoter, CD3 promoter, immunoglobulin light or heavy chain promoters, neurofiliment promoter, neuron specific enolase promoter, L7 promoter, CD2 promoter, myosin light chain kinase promoter, HOX gene promoter, thymidine kinase (TK) promoter, RNA Pol II promoter, MYOD promoter, MYF5 promoter, phosphoglycerokinase (PGK) promoter, Stf1 promoter, Low Density Lipoprotein (LDL) promoter, chicken b-actin promoter (used in conjunction with ecdysone response element), and the like.

As readily understood by those of skill in the art, the term "tissue specific" refers to the substantially exclusive initiation of transcription in the tissue from which a particular promoter that drives expression of a given gene is derived (e.g., expressed only in T-cells, endothelial cells, smooth muscle cells, and the like). Exemplary tissue specific promoters contemplated for use in the practice of the present invention include the GH promoter, the NSE promoter, the GFAP promoter, neurotransmitter promoters (e.g., tyrosine hydroxylase, TH, choline acetyltransferase, ChAT, and the like), promoters for neurotropic factors (e.g., a nerve growth factor promoter, NT-3, BDNF promoters, and the like), and so on.

As used herein, when referring to nucleic acids, the phrase "exogenous to said mammalian host" or simply "exogenous" refers to nucleic acids not naturally found at levels sufficient to provide a function in the particular cell where transcription is desired. For example, exogenous nucleic acids can be either natural or synthetic nucleic acids, which are introduced into the host in the form of DNA or RNA. The nucleic acids of interest can be introduced into target cells (for in vitro applications), or the nucleic acids of interest can be introduced directly or indirectly into a host, for example, by the transfer of transformed cells into a host.

In contrast to exogenous nucleic acids, the phrase "endogenous nucleic acids" or "endogenous genes" refers to nucleic acids naturally found at levels sufficient to provide a function in the particular cell where transcription is desired.

Exogenous nucleic acids contemplated for use in the practice of the present invention include wild type and/or therapeutic nucleic acids. "Wild type" genes are those that are native to cells of a particular type. Exemplary wild type nucleic acids are genes which encode products the substantial absence of which leads to the occurrence of a non-normal state in a host; or a substantial excess of which leads to the occurrence of a non-normal state in a host.

Such genes may not be expressed in biologically significant levels or may be undesirably overexpressed. Thus, for example, while a synthetic or natural gene coding for human insulin would be exogenous genetic material to a yeast cell (since yeast cells do not naturally contain insulin genes), a human insulin gene inserted into a human skin fibroblast cell would be a wild type gene with respect to the fibroblast since human skin fibroblasts contain genetic material encoding human insulin, although human skin fibroblasts do not express human insulin in biologically significant levels.

Therapeutic nucleic acids contemplated for use in the practice of the present invention include those which encode products which are toxic to the cells in which they are expressed; or encode products which impart a beneficial property to a host; or those which transcribe nucleic acids which modulate transcription and/or translation of endogenous genes.

As employed herein, the phrase "therapeutic nucleic acids" refers to nucleic acids that impart a beneficial function to the host in which such nucleic acids are transcribed. Therapeutic nucleic acids are those that are not naturally found in host cells. For example, synthetic or natural nucleic acids coding for wild type human insulin would be therapeutic when inserted into a skin fibroblast cell so as to be expressed in a human host, where the human host is not otherwise capable of expressing functionally active human insulin in biologically significant levels. Further examples of therapeutic nucleic acids include nucleic acids that transcribe antisense constructs used to suppress the expression of endogenous genes. Such antisense transcripts bind endogenous nucleic acid (mRNA or DNA) and effectively cancel out the expression of the gene. In accordance with the methods described herein, therapeutic nucleic acids are expressed at a level that provides a therapeutically effective amount of the corresponding therapeutic protein.

Exogenous nucleic acids useful in the practice of the present invention include genes that encode biologically active proteins of interest, such as, e.g., secretory proteins that can be released from said cell; enzymes that can metabolize a toxic substance to produce a non-toxic substance, or that metabolize an inactive substance to produce a useful substance; regulatory proteins; cell surface receptors; and the like. Useful genes include genes that encode blood clotting factors, such as human factors VIII and IX; genes that encode hormones, such as insulin, parathyroid hormone, luteinizing hormone releasing factor (LHRH), alpha and beta seminal inhibins, and human growth hormone; genes that encode proteins, such as enzymes, the absence of which leads to the occurrence of an abnormal state; genes encoding cytokines or lymphokines such as interferons, granulocytic macrophage colony stimulating factor (GM-CSF), colony stimulating factor-1 (CSF-1), tumor necrosis factor (TNF), and erythropoietin (EPO); genes encoding inhibitor substances such as alpha$_1$-antitrypsin; genes encoding substances that function as drugs, e.g., genes encoding the diphtheria and cholera toxins; and the like.

Additional nucleic acids contemplated for use in accordance with the present invention include genes that encode proteins present in dopaminergic neurons (useful, for example, for the treatment of Parkinson's disease), cholinergic neurons (useful, for example, for the treatment of Alzheimer's disease), hippocampal pyramidal neurons (also useful for the treatment of Alzheimer's disease), norepinephrine neurons (useful, for example, for the treatment of epilepsy), spinal neurons (useful, for example, for the treatment of spinal injury), glutamatergic neurons (useful, for example, for the treatment of schizophrenia), cortical neurons (useful, for example, for the treatment of stroke and brain injury), motor and sensory neurons (useful, for example, for the treatment of amyotrophic lateral sclerosis), and the like.

Typically, nucleic acid sequence information for proteins encoded by exogenous nucleic acid(s) contemplated for use employed herein can be located in one of many public access databases, e.g., GENBANK, EMBL, Swiss-Prot, and PIR, or in related journal publications. Thus, those of skill in the art have access to sequence information for virtually all known genes. Those of skill in the art can obtain the corresponding nucleic acid molecule directly from a public depository or from the institution that published the sequence. Optionally, once the nucleic acid sequence encoding a desired protein has been ascertained, the skilled artisan can employ routine methods, e.g., polymerase chain reaction (PCR) amplification, to isolate the desired nucleic acid molecule from the appropriate nucleic acid library. Thus, all known nucleic acids encoding proteins of interest are available for use in the methods and products described herein.

Additional components that can optionally be incorporated into the invention constructs include selectable markers and genes encoding proteins required for retroviral packaging, e.g., the pol gene, the gag gene, the env gene, and the like.

Selectable markers contemplated for use in the practice of the present invention include antibiotic resistance genes, genes that enable cells to process metabolic intermediaries, and the like. Exemplary antibiotic resistance genes include genes which impart tetracycline resistance, genes that impart ampicillin resistance, neomycin resistance, hygromycin resistance, puromycin resistance, and the like.

Genes that enable cells to process metabolic intermediaries include genes which permit cells to incorporate L-histidinol, genes encoding thymidine kinase, genes encoding xanthine-guanine phosphoribosyl transferase (gpt), genes encoding dihydrofolate reductase, genes encoding asparagine synthetase, and the like.

As employed herein, the terms "subject organism" and "host" refer to the cell, tissue, organ or organism in need of transcriptional regulation of exogenous or endogenous nucleic acids. The subject organism can be mammalian or mammalian-derived cells or tissue. Exemplary mammals include: humans; domesticated animals, e.g., rat, mouse, rabbit, canine, feline, and the like; farm animals, e.g., chicken, bovine, ovine, porcine, and the like; animals of zoological interest, e.g., monkey, baboon, and the like, or a cell thereof. Alternatively, a subject organism can be a non-mammalian, preferably non-insect, such as a plant, fungus or other non-mammalian species, or a cell of such a non-mammalian species.

As employed herein, the term "ligand" (or ligand precursor) refers to a steroidal or non-steroidal substance or compound which, in its native state (or after conversion to its "active" form), binds to at least one of the protein units, or to the invention chimeric protein, thereby creating a ligand/functional entity complex, which in turn can bind an appropriate response element and activate transcription therefrom. Ligands function to modulate transcription of nucleic acid(s) maintained under the control of a response element. Such ligands are well known in the art.

In accordance with one aspect of the present invention, unless and until a suitable ligand is administered to the host, substantially no transcription of the desired exogenous nucleic acids occurs. Since ecdysteroids, for example, are not naturally present in mammalian, plant and fungal systems, and the like, if it is desired that transcription of a particular exogenous nucleic acid be under precise control of the practitioner, a chimeric protein containing an ecdysone receptor as one of the protein units and a suitable dimer partner therefore is used and the exogenous nucleic acid is put under the control of an ecdysone response element, i.e. a response element to which an activated ecdysone receptor binds in nature.

The terms "ecdysone" and "ecdysteroid" as interchangeably used herein, are employed in the generic sense (in accordance with common usage in the art), referring to a family of ligands with the appropriate binding and transactivation activity (see, for example, Cherbas et al., in *Biosynthesis, metabolism and mode of action of invertebrate hormones* (Ed. J. Hoffmann and M. Porchet), Springer-Verlag, Berlin, p 305–322. An ecdysone, therefore, is a compound which acts to modulate gene transcription for a gene maintained under the control of an ecdysone response element.

20-Hydroxy-ecdysone (also known as β-ecdysone) is the major naturally occurring ecdysone. Unsubstituted ecdysone (also known as α-ecdysone) is converted in peripheral tissues to β-ecdysone. Analogs of the naturally occurring ecdysones are also contemplated within the scope of the present invention. Examples of such analogs, commonly referred to as ecdysteroids, include ponasterone A, 26 iodoponasterone A, muristerone A, inokosterone, 26-mesylinokosterone, and the like. Since it has been previously reported that the above-described ecdysones are neither toxic, teratogenic, nor known to affect mammalian physiology, they are ideal candidates for use as inducers in cultured cells and transgenic mammals according to the invention methods.

Other phytoecdysteroids are also contemplated for use in the practice of the invention as ligands of receptors which recognizes ecdysone response elements. Such phytoecdysteroids are known in the art (J. H. Adler et al., *Lipids* 30(3):257–62, 1995). The biological effect of phytoecdysteroids in higher animals are also known (V. N. Syrov, *Eksp. Klin. Farmakol.* 57(5):61–6, 1994).

Non-steroidal ligands are also contemplated for use in the practice of the present invention as ligands of ecdysone response elements. For example, when a ligand not normally present in the cells of the host to be treated is desired (i.e., a ligand exogenous to the host), a hydrazine can be employed as the ligand, preferably a diacyl hydrazine. Such hydrazines include compounds that are readily available and/or are relatively inexpensive to manufacture. One such compound, tebufenozide, is a non-steroidal ecdysone agonist which is commercially available. This compound specifically targets lepidopteran species, including *Bombyx mori*. Tebufenozide has undergone extensive testing in animal hosts and has proved to be of very low toxicity to mammals and other non-insect species.

Additional exemplary hydrazines contemplated for use herein include 1,2-diacyl hydrazines (e.g., tebufenozide), N'-substituted-N,N'-disubstituted hydrazines, dibenzoylalkyl cyanohydrazines, N-substituted-N-alkyl-N,N-diaroyl hydrazines, N-substituted-N-acyl-N-alkyls, carbonyl hydrazines, N-aroyl-N'-alkyl-N'-aroyl hydrazines, and the like. Since it has been previously reported that the above-described diacyl hydrazines are neither toxic, teratogenic, nor known to affect mammalian physiology, they are ideal candidates for use as exogenic ligands (e.g. as inducers) in cultured cells and transgenic mammals according to invention methods.

Ligands, and formulations containing them, administered in a manner compatible with the route of administration, the dosage formulation, and in a therapeutically effective amount. The required dosage will vary with the particular treatment desired, the degree and duration of therapeutic effect desired, the judgment of the practitioner, as well as properties peculiar to each individual. Moreover, suitable dosage ranges for systemic application depend on the route of administration. It is anticipated that dosages between about 10 micrograms and about 1 milligram per kilogram of body weight per day will be used for therapeutic treatment.

An effective amount of ligand contemplated for use in the practice of the present invention is the amount of ligand (e.g., diacyl hydrazine(s)) required to achieve the desired level of transcription and/or translation of exogenous nucleic acid. A therapeutically effective amount is typically an amount of ligand or ligand precursor that, when administered in a physiologically acceptable composition, is sufficient to achieve a plasma concentration of the transcribed or expressed nucleic acid product from about 0.1 mg/ml to about 100 mg/ml, for example, from about 1.0 mg/ml to about 50 mg/ml, and preferably at least about 2 mg/mil and usually 5 to 10 mg/ml.

Ligand can be administered in a variety of ways, as are well-known in the art, i.e., by any means that produces contact between ligand and receptor peptide. For example, such ligands can be administered topically, orally, intravenously, intraperitoneally, intravascularly, and the like. The administration can be by any conventional means available for use in conjunction with pharmaceuticals, e.g., by intravenous injection, either as individual therapeutically active ingredients or in a combination with other therapeutically active ingredients. Ligands contemplated for use in the practice of the present invention can be administered alone, but are generally administered with a pharmaceutical carrier selected on the basis of the chosen route of administration and standard pharmaceutical practice.

In accordance with a particular embodiment of the present invention, pharmaceutically acceptable formulations, and kits thereof, comprising at least one ligand for an invention functional dimer, for example an ecdysteroid, and a pharmaceutically acceptable carrier are contemplated. In accordance with another aspect of the present invention, pharmaceutically acceptable formulations consisting essentially of at least one ligand and a pharmaceutically acceptable carrier, are contemplated. Pharmaceutical formulations of the present invention can be used in the form of a solid, a solution, an emulsion, a dispersion, a micelle, a liposome, and the like, wherein the resulting formulation contains one or more of the ligands of the present invention, as an active ingredient, in admixture with an organic or inorganic carrier or excipient suitable for enteral or parenteral applications.

The ligand(s) may be compounded, for example, with the usual non-toxic, pharmaceutically acceptable carriers suitable for administration by oral, topical, nasal, transdermal, intravenous, subcutaneous, intramuscular, intracutaneous, intraperitoneal, intravascular, and the like means. Administration in the form of creams, lotions, tablets, dispersible powders, granules, syrups, elixirs, sterile aqueous or non-aqueous solutions, suspensions or emulsions, and the like, is contemplated. Exemplary pharmaceutically acceptable carriers include carriers for tablets, pellets, capsules, suppositories, solutions, emulsions, suspensions, and any other form suitable for use. Such carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and/or perfumes may be used. The active compound (e.g., ecdysteroid as described herein) is included in the pharmaceutically acceptable formulation in an amount sufficient to produce the desired effect upon the process or condition of diseases.

Pharmaceutically acceptable formulations containing ligand(s) as active ingredient may be in a form suitable for oral use, for example, as aqueous or oily suspensions, syrups or elixirs, tablets, troches, lozenges, dispersible powders or granules, emulsions, or hard or soft capsules. For the preparation of oral liquids, suitable carriers include emulsions, solutions, suspensions, syrups, and the like, optionally containing additives such as wetting agents, emulsifying and suspending agents, dispersing agents, sweetening, flavoring, coloring, preserving and perfuming agents, and the like. Formulations intended for oral use may be prepared according to any method known to the art for the manufacture of pharmaceutically acceptable formulations.

Tablets containing ligand(s) as active ingredient in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874, to form osmotic therapeutic tablets for controlled release.

In some cases, formulations for oral use may be in the form of hard gelatin capsules wherein the ligand is mixed with an inert solid diluent, for example, calcium carbonate, calcium phosphate or kaolin. They may also be in the form of soft gelatin capsules wherein the ligand is mixed with water or an oil medium, for example, peanut oil, liquid paraffin, or olive oil.

The pharmaceutically acceptable formulations may be in the form of a sterile injectable suspension. Suitable carriers include non-toxic parenterally-acceptable sterile aqueous or non-aqueous solutions, suspensions, or emulsions. This suspension may be formulated according to known methods using suitable dispersing or wetting agents and suspending agents. They can also be manufactured in the form of sterile water, or some other sterile injectable medium immediately before use. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. They may be sterilized, for example, by filtration through a bacteria-retaining filter, by incorporating sterilizing agents into the formulations, by irradiating the formulations, or by heating the formulations. Sterile injectable suspensions may also contain adjuvants such as preserving, wetting, emulsifying, and dispersing agents. Buffers, preservatives, antioxidants, and the like can be incorporated as required.

Compounds contemplated for use in the practice of the present invention may also be administered in the form of suppositories for rectal administration of the drug. These formulations may be prepared by mixing the drug with a suitable non-irritating excipient, such as cocoa butter, synthetic glyceride esters of polyethylene glycols, which are solid at ordinary temperatures, but liquefy and/or dissolve in the rectal cavity to release the drug.

Pharmaceutically acceptable formulations containing suitable ligand(s) are preferably administered intravenously, as by injection of a unit dose, for example. The term "unit dose," when used in reference to a pharmaceutically acceptable formulation of the present invention, refers to a quantity of the pharmaceutical formulation suitable as unitary dosage for the subject, each unit containing a predetermined quantity of active material calculated to produce the desired therapeutic effect in association with the required diluent, i.e., carrier, or vehicle. It may be particularly advantageous to administer such formulations in depot or long-lasting form as discussed hereinafter.

Therapeutic compositions or pharmaceutically acceptable formulations containing suitable ligand are preferably administered intravenously, as by injection of a unit dose, for example. The term "unit dose," when used in reference to a therapeutic composition of the present invention, refers to a quantity of ligand suitable as unitary dosage for the subject, each unit containing a predetermined quantity of active material calculated to produce the desired therapeutic effect in association with the required diluent, i.e., carrier, or vehicle. It may be particularly advantageous to administer such compounds in depot or long-lasting form.

Suitable regimes for initial administration and booster shots are variable, but are typified by an initial administration followed by repeated doses at one or more intervals, by a subsequent injection, or other administration. Alternatively, continuous intravenous infusion sufficient to maintain concentrations in the blood in the ranges specified for in vivo therapies are contemplated.

In accordance with another embodiment of the present invention, there are provided methods for producing transgenic animals capable of prolonged and regulated expression of exogenous nucleic acid(s), said method comprising introducing into early-stage embryos or stem cells of the animal:
 (i) a nucleic acid construct comprising a promoter and said exogenous nucleic acid(s) under the control of a regulatory element; and
 (ii) nucleic acid encoding an invention chimeric protein wherein the chimeric protein activates the regulatory element in the presence of a ligand for the functional dimer or represses the regulatory element independently of the presence of said ligand.

As used herein, the phrase "transgenic animal" refers to an animal that contains one or more expression constructs containing one or more exogenous nucleic acid(s) under the transcription control of an operator and/or hormone response element as described herein.

Methods of making transgenic animals using a particular nucleic acid construct are well-known in the art. When preparing invention transgenic animals, it is presently preferred that two transgenic lines are generated. The first line will express, for example, a chimeric protein as described above (e.g., VBEcR). Tissue specificity is conferred by the selection of a tissue-specific promoter (e.g., T-cell specific) that will direct expression of the chimeric protein to appropriate tissue. A second line contains a nucleic acid construct comprising a promoter and exogenous nucleic acid under the control of a response element, for example, an endogenous response element. Cross-breeding of these two lines will provide a transgenic animal that expresses an invention chimeric protein and the exogenous nucleic acid.

In a presently preferred embodiment, an invention transgenic animal contains one or more expression constructs containing nucleic acid encoding an invention chimeric protein and exogenous nucleic acid under the transcription control of a response element. Thus, with tissue specific expression of the chimeric protein as described above and timely ligand treatment, gene expression can be induced or repressed with spatial, dosage, and/or temporal specificity.

In accordance with yet another embodiment of the present invention, there are provided methods for modulating the transcription of an exogenous nucleic acid in a host containing:
 (i) a nucleic acid construct comprising a promoter and said exogenous nucleic acid(s) under the control of a response element; and
 (ii) nucleic acid under the control of an inducible promoter, said nucleic acid encoding an invention chimeric protein wherein the functional entity formed by the invention chimeric protein activates or represses the response element in the presence of a ligand for the entity; and
  said method comprising introducing a ligand not normally present in the cells of the host and subjecting the host to conditions suitable to induce or repress expression of the invention chimeric protein.

In accordance with yet another embodiment of the present invention, there are provided methods for the expression of recombinant products detrimental to a subject organism, said method comprising:
 transforming suitable cells in the organism with:
  (i) a nucleic acid construct comprising a promoter and exogenous nucleic acid(s) which express the recombinant product under the control of a regulatory element that is not normally present in the cells of said organism, and
  (ii) nucleic acid encoding an invention chimeric protein wherein the functional entity formed by the invention chimeric protein activates the regulatory element in the presence of a ligand for the functional entity;
 growing said cells to the desired level in the substantial absence of the ligand; and
 inducing expression of said recombinant product by administering to the organism a ligand, which, in combination with said entity, binds to said regulatory element and activates transcription therefrom.

Recombinant products detrimental to a host organism contemplated for expression in accordance with the present invention include any gene product that functions to confer a toxic effect on the organism. For example, inducible expression of a toxin such as the diphtheria toxin would allow for specific ablation of tissue (Ross et al. *Genes and Development* 7:1318–1324 (1993)), for example to create a new phenotype in the transgenic animal. Moreover, the numerous gene products that are known to induce apoptosis in cells expressing such products are contemplated for use herein (see, e.g, Apoptosis, *The Molecular Basis of Cell Death*, Current Communications In Cell & Molecular Biology, Cold Spring Harbor Laboratory Press, 1991).

In accordance with still another embodiment of the present invention, there are provided methods for modulating the transcription of nucleic acid(s) in an in vitro cellular system, wherein the method comprises administering to the cellular system an amount of ligand effective to modulate the transcription of the nucleic acid(s); wherein the ligand is not normally present in the cellular system and wherein the system comprises:
 (i) a nucleic acid construct comprising a promoter and the nucleic acid(s) under the control of a response element; and
 (ii) nucleic acid encoding an invention chimeric protein, wherein the functional entity formed by the invention chimeric protein activates or represses the regulatory element in the presence of a ligand for the ligand binding domain.

In accordance with yet another embodiment of the present invention, there are provided methods for the treatment of a host in need of gene therapy, said method comprising:
 introducing into cells of said host:
  (i) a nucleic acid construct comprising a promoter and the exogenous nucleic acid(s) under the control of a response element;
  (ii) nucleic acid under the control of an inducible promoter, said nucleic acid encoding an invention chimeric protein,
   wherein the functional dimer formed by the invention chimeric protein activates or represses the regulatory element in the presence of a ligand for the functional dimer, and administering, to said host, an effective amount of ligand for the invention functional dimer.

Optionally, the cells can be obtained from the host, modified as above, and then reintroduced into the host organism. For example, the exogenous nucleic acid can be introduced directly into cells obtained from a donor (host or separate donor) and the modified cells are then implanted within the host organism. In a presently preferred embodiment, the transplanted cells are autologous with respect to the host. "Autologous" means that the donor and recipient of the cells are one and the same.

Cells can be modified by "in vivo delivery" of biological materials by such routes of administration as oral, intravenous, subcutaneous, intraperitoneal, intrathecal, intramuscular, intracranial, inhalational, topical, transdermal, suppository (rectal), pessary (vaginal), and the like. The exogenous nucleic acid may be stably incorporated into cells or may be transiently expressed using methods known in the art.

Modified cells are cultivated under growth conditions (as opposed to protein expression conditions) until a desired density is achieved. Stably transfected mammalian cells may be prepared by transfecting cells with an expression vector having a selectable marker gene (such as, for example, the gene for thymidine kinase, dihydrofolate reductase, neomycin resistance, and the like), and growing the transfected cells under conditions selective for cells expressing the marker gene. To prepare transient transfectants, mammalian cells are transfected with a reporter gene (such as the *E. coli* β-galactosidase gene) to monitor transfection efficiency. Selectable marker genes are typically not included in the transient transfections because the transfectants are typically not grown under selective conditions, and are usually analyzed within a few days after transfection.

The concept of gene replacement therapy for humans involves the introduction of functionally active "wild type" or "therapeutic" nucleic acids into the somatic cells of an affected host to correct a gene defect or deficiency. However, in order for gene replacement therapy to be effective, it must be possible to control the time and location at which gene expression occurs.

Genes that encode useful "gene therapy" proteins that are not normally transported outside the cell can be used in the invention if such genes are "functionally appended" to, or operatively associated with, a signal sequence that can "transport" the encoded product across the cell membrane. A variety of such signal sequences are known and can be used by those skilled in the art without undue experimentation.

Gene transfer vectors (also referred to as "expression vectors") contemplated for use herein are recombinant nucleic acid molecules that are used to transport nucleic acid into host cells for expression and/or replication thereof. Expression vectors may be either circular or linear, and are capable of incorporating a variety of nucleic acid constructs therein. Expression vectors typically come in the form of a plasmid that, upon introduction into an appropriate host cell, results in expression of the inserted nucleic acid.

Suitable expression vectors for use herein are well known to those of skill in the art and include recombinant DNA or RNA construct(s), such as plasmids, phage, recombinant virus or other vectors that, upon introduction into an appropriate host cell, result(s) in expression of the inserted DNA. Appropriate expression vectors are well known to those of skill in the art and include those that are replicable in eukaryotic cells and/or prokaryotic cells and those that remain episomal or those which integrate into the host cell genome. Expression vectors typically further contain other functionally important nucleic acid sequences encoding antibiotic resistance proteins, and the like.

The amount of exogenous nucleic acid introduced into a host organism, cell or cellular system can be varied by those of skill in the art. For example, when a viral vector is employed to achieve gene transfer, the amount of nucleic acid introduced can be varied by varying the amount of plaque forming units (PFU) of the viral vector.

As used herein, the phrase "transcription regulatory region" refers to that portion of a nucleic acid or gene construct that controls the initiation of mRNA transcription. Regulatory regions contemplated for use herein, in the absence of the non-mammalian transactivator, typically comprise at least a minimal promoter in combination with a regulatory element responsive to the ligand/receptor peptide complex. A minimal promoter, when combined with a regulatory element, functions to initiate mRNA transcription in response to a ligand/functional dimer complex. However, transcription will not occur unless the required inducer (ligand therefor) is present. However, as described herein certain of the invention chimeric protein heterodimers activate or repress mRNA transcription even in the absence of ligand for the DNA binding domain.

As used herein, the phrase "operatively associated with" refers to the functional relationship of DNA with regulatory and effector sequences of nucleotides, such as promoters, enhancers, transcriptional and translational stop sites, and other signal sequences. For example, operative linkage of DNA to a promoter refers to the physical and functional relationship between the DNA and promoter such that the transcription of such DNA is initiated from the promoter by an RNA polymerase that specifically recognizes, binds to and transcribes the DNA.

Preferably, the transcription regulatory region further comprises a binding site for ubiquitous transcription factor(s). Such binding sites are preferably positioned between the promoter and the regulatory element. Suitable ubiquitous transcription factors for use herein are well-known in the art and include, for example, Sp1.

Exemplary eukaryotic expression vectors include eukaryotic constructs, such as the pSV-2 gpt system (Mulligan et al., (1979) *Nature*, 277:108–114); pBlueSkript (Stratagene, La Jolla, Calif.), the expression cloning vector described by Genetics Institute (*Science*, (1985) 228:810–815), and the like. Each of these plasmid vectors is capable of promoting expression of the chimeric protein of interest.

Suitable means for introducing (transducing) expression vectors containing invention nucleic acid constructs into host cells to produce transduced recombinant cells (i.e., cells containing recombinant heterologous nucleic acid) are well-known in the art (see, for review, Friedmann, *Science*, 244:1275–1281, 1989; Mulligan, *Science*, 260:926–932. 1993, each of which are incorporated herein by reference in their entirety). Exemplary methods of transduction include, e.g., infection employing viral vectors (see, e.g., U.S. Pat. Nos. 4,405,712 and 4,650,764), calcium phosphate transfection (U.S. Pat. Nos. 4,399,216 and 4,634,665), dextran sulfate transfection, electroporation, lipofection (see, e.g., U.S. Pat. Nos. 4,394,448 and 4,619,794), cytofection, particle bead bombardment, and the like. The transduced nucleic acid can optionally include sequences which allow for its extrachromosomal (i.e., episomal) maintenance, or the transduced nucleic acid can be donor nucleic acid that integrates into the genome of the host.

In a specific embodiment, a gene transfer vector contemplated for use herein is a viral vector, such as Adenovirus, adeno-associated virus, a herpes-simplex virus based vector, a synthetic vector for gene therapy, and the like (see, e.g., Suhr et al., *Arch. of Neurol.* 50:1252–1268, 1993). Preferably, a gene transfer vector employed herein is a retroviral vector. Retroviral vectors contemplated for use herein are gene transfer plasmids that have an expression construct containing an exogenous nucleic acid residing between two retroviral LTRs. Retroviral vectors typically contain appropriate packaging signals that enable the retroviral vector, or RNA transcribed using the retroviral vector as a template, to be packaged into a viral virion in an appropriate packaging cell line (see, e.g., U.S. Pat. No. 4,650,764).

Suitable retroviral vectors for use herein are described, for example, in U.S. Pat. Nos. 5,399,346 and 5,252,479; and in WIPO publications WO 92/07573, WO 90/06997, WO 89/05345, WO 92/05266 and WO 92/14829, each of which is hereby incorporated herein by reference, in its entirety. These documents provide a description of methods for efficiently introducing nucleic acids into human cells using such retroviral vectors. Other retroviral vectors include, for example, mouse mammary tumor virus vectors (e.g., Shackleford et al., (1988) *PNAS, USA*, 85:9655–9659), human immunodeficiency virus (e.g., Naldini et al. (1996) *Science* 272:165–320), and the like.

Various procedures are also well-known in the art for providing helper cells which produce retroviral vector particles that are essentially free of replicating virus. See, for example, U.S. Pat. No. 4,650,764; Miller, *Human Gene Therapy*, 1:5–14, 1990; Markowitz, et al., *Journal of Virology*, 61(4):1120–1124, 1988; Watanabe, et al., *Molecular and Cellular Biology*, 3(12):2241–2249, 1983; Danos, et al., *PNAS*, 85:6460–6464, 1988; and Bosselman, et al., *Molecular and Cellular Biology*, 7(5):1797–1806, 1987, which disclose procedures for producing viral vectors and helper cells that minimize the chances for producing a viral vector that includes a replicating virus.

Recombinant retroviruses suitable for carrying out the invention methods are produced employing well-known methods for producing retroviral virions. See, for example, U.S. Pat. No. 4,650,764; Miller, supra 1990; Markowitz, et al., supra 1988; Watanabe, et al., supra 1983; Danos, et al., *PNAS*, 85:6460–6464, 1988; and Bosselman, et al., *Molecular and Cellular Biology*, 7(5):1797–1806, 1987.

For example, in one embodiment, a modular assembly retroviral vector (MARV) can be utilized to express the invention chimeric protein and an antibiotic resistance gene. A "covector" (referred to herein as MARSHA) can be utilized to provide a nucleic acid construct comprising the promoter, the regulatory element and exogenous nucleic acid, and a second antibiotic resistance gene. The MARSHA vector carrying exogenous nucleic acid also has LTRs modified to promote high-level expression only in the presence of the invention chimeric protein encoded by MARV and exogenous ligand therefor. Co-infected primary mammalian cells can then be selected using both antibiotics, resulting in a cell population that is dependent on ligand for high-level expression of the exogenous nucleic acid.

By introducing all of the necessary regulatory machinery, plus exogenous nucleic acid, selectable markers, and nucleic acid encoding invention chimeric protein, e.g., into a MARV retrovirus, highly efficient insertion of exogenous nucleic acids into targeted cells can be achieved.

Thus, the above-described viral constructs address several important problems confronted in the use of retroviruses in application of therapeutic gene transfer strategies to a variety of human diseases. For example, the retroviral vectors of the invention are capable of prolonged gene expression under conditions where conventionally integrated retroviruses are no longer transcriptionally active.

To illustrate the invention chimeric protein FDs, EcR was used as the steroid/thyroid hormone nuclear receptor and multiple examples using either RXR or Usp as the dimer partner were constructed, with either the EcR or the dimer partner positioned at the amino terminus. The DNA binding, transactivation, and dimerization properties of these several FD variants were compared with the properties of native receptor complexes. The size of the ENU and ENR FDs prepared was in the range from about 135 to about 145 kD; whereas E alone had a size of 94 kD, as shown by Western blot analysis.

EcR-Usp and EcR-RXR FDs Efficiently Bind EcREs

The FDs were first examined for their ability to bind to target EcREs in response to ligand. FD proteins were extracted from transiently transfected human 293 cells that were either untreated or treated with 1 μM murA for 40 hours. To eliminate the possibility that certain of the FD constructs were translated with greater efficiency than others, which would lead to a false appearance of higher functional binding in comparative luciferase expression tests, β-galactosidase expression of internal control plasmids cotransfected with FD constructs was performed. These tests indicated no significant differences in the transfection efficiency of individual FD constructs, indicating that the DNA binding differences observed for different FDs reflect intermolecular properties of the FDs themselves, not expression level. Accordingly, all reactions were normalized to an internal β-galactosidase control and total protein using the anti-EcR monoclonal antibody DDA2.7 (Koelle et al., supra, 1991).

Figure 2B:
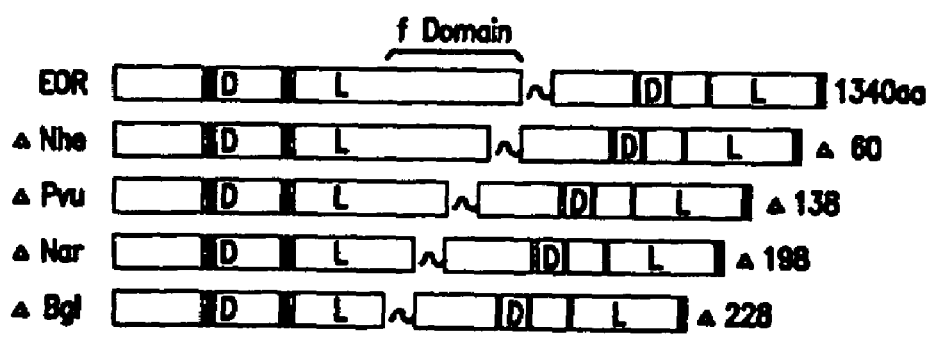

FD constructs with either 0 or 5 linker segments were assayed for their ability to bind labeled EcREs, as shown in FIG. 2B. A prominent band co-migrating with band shifts for the separate dimer complexes (E+U and E+R) was observed in many lanes and indicated that some of the FDs formed functional DNA-binding internal dimers, referred to herein as "endodimers." For example, R0E, which is analogous to U0E, except for the substitution of U for R as the dimer partner, formed a clear endodimer band that was increased 4-fold by ligand, and demonstrated unequivocally a response to hormone. R5E, with a longer linker, had slightly decreased basal, and slightly increased ligand-stimulated, EcRE binding (5-fold) compared to that of R0E.

Constructs in which E is positioned at the N-terminus form endodimers and bind the EcRE probe an average of 10 times better than UNE constructs (FIG. 2A). In addition, ENU constructs bind probe 80–150% more readily than even those other FDs with high-level EcRE binding, such as E5R, but display nearly complete insensitivity to ligand for formation of DNA-binding complexes. This effect was found to be substantially independent of linker length.

ENR FDs also demonstrate a greater affinity for the EcRE probe than do RNE constructs. However, unlike ENU constructs, ENR FDs have a high degree of dependence upon the presence of ligand for formation of endodimers.

The observation that ENU and ENR FDs bound probe better than either the RNE construct or the UNE construct prompted examination of whether the large 220 amino acid F domain of E (not found on R or U) accounted for this effect. Further EcRE probe binding studies performed utilizing several FDs having in-frame incremental deletions of EOR to NheI, PvuII, NarI, and BglII sites within the ecdysone receptor F domain (FIG. 2B) showed that the deletions had a minimal effect on either response to ligand, or on binding to the EcRE probe. Only EOR-ΔBglII, in which the extreme C-terminal end of the hormone binding domain is removed, displayed significant loss of the shifted band. These results suggest that flexibility within the long EcR F domain is not the primary determinant of improved DNA binding by FDs containing a EcR at the N terminal. This was presumed to be the result of a perturbed ligand binding pocket as opposed to decreased flexibility of the dimer partners joined by a linker.

EcR-RXR and EcR-Usp FD Transactivation in Response to Ligand

The results shown in FIG. 2 clearly indicate that the EcR-RXR and EcR-Usp FD chimeric proteins could both respond to hormone and interact with the response element for EcR; however, these tests provided no indication regarding the function of these proteins to transactivate responsive promoters and induce gene expression. To determine the ability of the FDs to transactivate responsive promoters and induce gene expression, the FDs and an EcRE-luciferase reporter plasmid were co-transfected into 293 cells. The results of these studies revealed that the activity of the FDs was variably diminished compared to that of monomeric receptors.

Figure 5A:
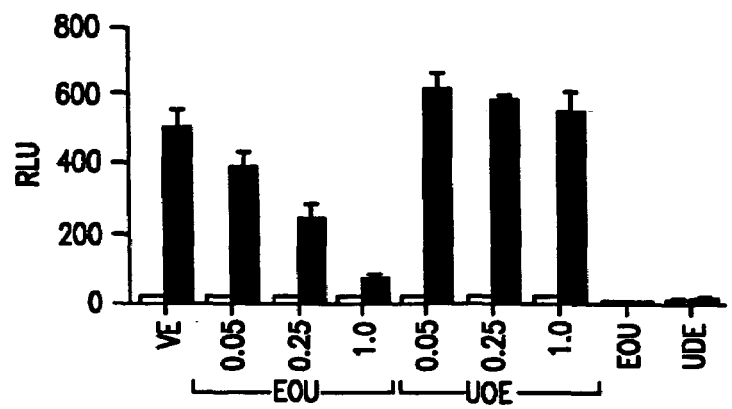
FIG. 5A shows a comparison of the inhibitory effects of E0U and U0E on ligand-stimulated expression of luciferase by monomeric VE in combination with endogenous RXR. E0U and U0E without YE cotransfection are at the extreme right of the bar graph.
Figure 5B:
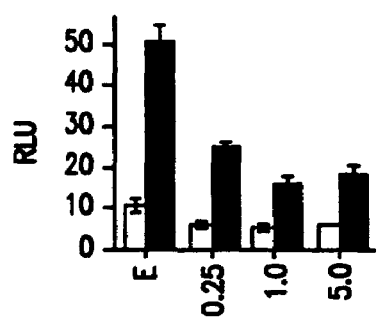
FIG. 5B shows the effects of monomeric EcR (without VP16 fusion) on ligand-stimulated expression of luciferase in the assay of FIG. 5A by competition with E0U or U0E.
Figure 5C:
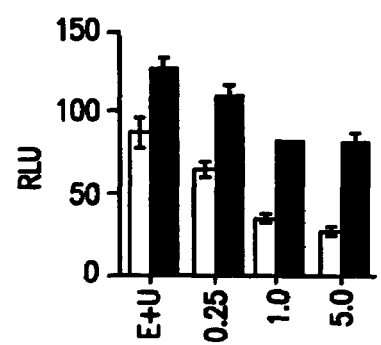
FIG. 5C shows the effects of monomeric EcR on luciferase expression in the presence of ligand in the assay of FIG. 5B, as compared with VE combined with monomeric exogenous Usp.

It has also been discovered that the invention ENU FDs are constitutive repressors of transcription of a gene under the control of the corresponding steroid/thyroid hormone nuclear receptor's response element. For example, UNE constructs did not efficiently bind target EcREs (FIG. 2), and predictably did not have a dramatic influence on expression of the E4-luc reporter plasmid. ENUs, on the other hand, although appearing to readily bind EcREs, were also unable to stimulate luciferase expression. To further confirm whether ENU proteins could bind target response elements, but had lost the capacity to transactivate, the ability of E0U to competitively block ligand-stimulated luciferase expression by monomeric receptors was tested. E0U elicited a dose-dependent inhibition of VE with endogenous dimer partner, whereas U0E had virtually no inhibitory influence (FIG. 5A). At the lowest ratio tested, a 1:20 ratio of E0U to VE decreased stimulated expression of VE by 20%, while equimolar E0U blocked 80% of the response to ligand. At any concentration tested, U0E exhibited no suppressive effect on VE-mediated activation, and in fact, appeared to increase the stimulated level of expression by about 5% to about 15%. E0U had a similar influence on E without VP16 fusion (FIG. 5B), and a lesser but measurable inhibitory effect on VE combined with separate exogenous Usp (FIG. 5C). The 50% inhibition of the VE+U basal transactivation level may suggest that E0U binds the target EcRE about as well as complexes of the separate receptors. The plateau of the E0U suppressive effect at a 1:1 ratio with both E and E+U and the slightly increased stimulation at a 5:1 ratio of E0U to separate receptors indicate that, at higher concentrations, E0U can weakly transactivate in response to added ligand.

In the experiments described herein utilizing FDs containing various combinations of DEcR and BEcR with either RXR or Usp, the length of the linker was not observed to have a significant effect on any of the functions of the FDs. Surprisingly, even shortening of the large F-domain of *Drosophilia melanogaster* EcR had little impact on ligand-responsive DNA binding of EcR FDs. Without restriction of the scope of the invention by any theoretical speculations, two possible explanations of this observation are offered. One possibility is that there is enough flexibility within the structure of the individual receptors that any deformation necessary to allow appropriate dimerization can be tolerated while preserving, in some cases, nearly complete activity. The second possibility is that the C-terminus of the 5' receptor naturally lies close in spatial proximity to the N-terminus of the 3' receptor such that the distance is easily spanned. In the absence of detailed structural data of intact nuclear hormone receptor dimers, neither explanation can be ruled out.

In the presence of ligand (i.e., MurA), RXR-containing FDs functioned similarly to monomeric ECR+RXR, but at approximately one-half of the maximum level of transactivation (for E5R). One likely explanation for this is that the FD constructs are expressed or translated less efficiently than the monomeric receptors as suggested by comparing the intensity of FD lanes to the E lane in a Western blot analysis. Although the level of absolute transactivation was halved, the relative induction of transcription by the ENR constructs, in particular, exceeded the relative induction of monomeric EcR and RXR.

To further address the partial or complete loss of transcriptional activation for FDs relative to the separate proteins, the powerful VP16 transactivating domain was coupled to the amino-termini of FDs or separate EcR to determine if this addition could restore lost transactivational capacity. While a linker containing 5 linker segments (65 amino acids) was sufficient to allow good DNA binding, it may not have allowed sufficient freedom of movement for other domains, including those responsible for transactivation, to fold or orient as they do in the native proteins. Length of the linkers in VE5R and VE5U was therefore increased in increments of 5 linker segments each to 10 and ultimately 20 linker segments (240+5 amino acids).

Addition of the VP16 activation domain to the amino terminus of the ENR FDs restored the full transactivation potential of the FDs relative to separate VP16-fused EcR, suggesting that addition of a strong transactivating domain overrides translational deficits caused by incorporating the receptor/dimer partner into a chimeric protein. However, VP16-ENU (VENU) chimeric proteins never exceeded 30% of the absolute level of transactivation of separate VE+U. One possible explanation is that some conformation constraint in the Usp half of the VENU constructs prevented the interaction of VENU with endogenous cofactors necessary for full high level expression. A second possibility is that increased spontaneous heterodimerization within ENU FDs results in a conformational alteration that decreases or blocks ligand binding, assuming that ligand plays a direct role in transactivation and not just dimerization.

Figure 3:
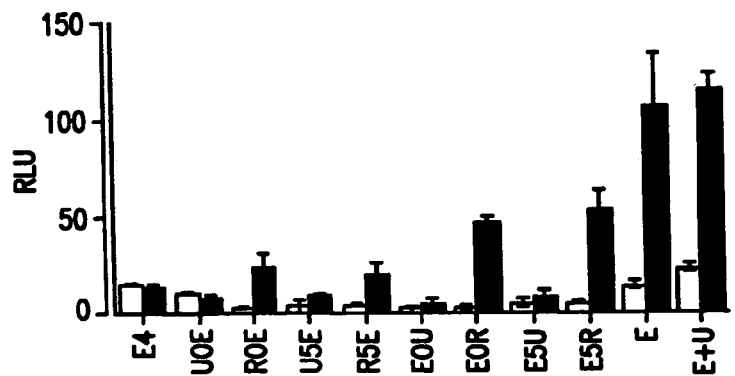
FIG. 3 is a graph showing relative luciferase expression induced by FD constructs with or without ligand as determined in transient transfection assays for FDs and for monomeric EcR with either Usp or RXR when treated with vehicle (open bars, i.e., −MurA) or 1 µM MurA (black bars, i.e., +MurA). Decimal numbers on the abscissa represent molar amount of FD relative to VE plasmid (1.0 is equimolar FD:VE). E0U and U0E without VE cotransfection are at the extreme right of the bar graph. See also Table 1.

High level VENR transactivation suggests that the very low level expression observed from unliganded ENR constructs in FIG. 3 was due to transcriptional repression by bound ENR proteins. The addition of VP16 increased the basal VENR FD expression over 5-fold in comparison to separate VECR+RXR. This presumably reflected an increased level of spontaneous dimer formation of ENR FDs resulting from the forced proximity of the separate components by the linker. This phenomenon may not have been readily evident in the gel shift experiments as the result of the short transient period of interaction of the proteins with the DNA probes (<30 minutes) compared to the duration with the responsive promoters in the transient transfection experiments (>30 hours).

Heterodimer Formation and DNA Binding of FDs

Five different classes of interaction of protein units in the invention chimeric protein(s) (FIG. 7) were predicted: 1) "disorganized", indicative of non-interaction by the individual receptor components; 2) "endodimer", indicating formation of functional dimers approximating the native heterodimer complex; 3) "trimer", indicating interaction with a separate monomeric partner, 4) "tetramer", indicative of two mutually cross-interacting chimeric proteins; or 5) "oligomers", representing chimeric proteins chain-interacting with each other. The data presented herein provides clear evidence that disorganized, endodimer, and trimer species were formed when the invention chimeric proteins contained two protein units (FDs), with endodimer formation predominating. Only the UNE constructs appeared to be largely disorganized, as evidenced by their apparent inability even to bind DNA with high affinity. All remaining FD classes showed abundant evidence of endodimer formation, although RNE constructs were noticeably weaker than constructs with EcR in the amino terminal position. The transient-transfection competition experiment (FIG. 4) indirectly indicates that a high affinity monomeric dimer partner, such as VUsp, can displace a weaker intramolecular RXR dimer partner to form a partially functional trimer species; however, such a monomeric, high affinity dimer partner was much less capable of displacing an intramolecular Usp under the same circumstances. The lower affinity VRXR monomeric dimer partner was unable to displace to any significant degree either Usp or RXR as an intramolecular dimer partner in an invention FD fusion protein.

Evidence of formation of higher order constructs, such as tetramers or oligomers, in gel shift assays is scant, but may be suggested in lanes of the gel shift assay with UNE and RNE constructs. Although band shifts were weak, UNE (and unliganded RNE) constructs had slightly intensified bands of higher molecular weight than the corresponding size of the endodimer bands. The faint but detectable high molecular weight shift bands observed for FDs in some lanes of the assays suggest tetramer and oligomer formation, presumably through cross interaction of the ecdysone receptor component of one FD with the dimer partner unit of another.

These results, coupled with the results of competition experiments using superphysiological levels of competing dimer partner, suggest, in any event, that multimerization is relatively rare and is likely to occur, at even low levels, only with those FDs that have decreased capacity for endodimer formation.

These data further support the supposition that proximity to dimer partner (i.e., as in invention chimeric protein(s)) not only limits dimer partner preference, but also increases the ease of dimer formation and DNA binding for some of the fusion constructs relative to monomeric receptors. For example, ENU constructs displayed high-level complex formation with the EcRE probe (a 1.1- and 0.9-fold increase for EU and E5U, respectively) even in the absence of ligand, while separate EcR and Usp required ligand for maximal complex formation. ENR constructs, on the other hand, still retained much of their original ligand dependence, indicating that dimer partner proximity is not the sole, or perhaps even most important, determinant of dimer formation.

The degree to which FDs interact with external receptors to form a trimer complex was indirectly examined in the studies showing their interaction with high levels of competing VP16-fusion dimer partners and the resulting effect on transactivation of the E4-luc reporter. In these studies, monomeric VRXR was unable to enter the FD complex of any construct, suggesting that the EcR component of FDs much prefers a linked dimer partner of either high or low affinity to a separate low affinity dimer partner. VUsp, on the other hand, had a comparatively smaller effect on transactivation induced by the E5U construct, than on E5R, indicating that the EcR protein in E5U preferentially dimerizes with the linked Usp, while the RXR dimer partner of E5R may enter a complex with monomeric VUsp.

In summary, the results of the studies described herein indicate that selected chimeric proteins of steroid/thyroid hormone nuclear receptors with appropriate dimer partners can retain most of the primary characteristics of the native complex: binding of ligand, recognition and binding of cognate response elements, and, in some cases, ligand-stimulated transactivation of responsive promoters. Subsets of the constructs prepared displayed varying degrees of these characteristics. The R/UNE proteins characteristically exhibited low DNA binding and transactivation capacity while the ENR/U proteins uniformly demonstrated wild-type or superior EcRE binding and variable capacity to transactivate, resulting in properties ranging from constitutive repression to essentially wildtype, ligand-responsive transactivation.

The invention herein provides the advantage that, for many studies in cultured cells or transgenic animals, invention FDs will allow the examination of specific heterodimer pairs with much decreased potential for contamination with exterior dimer partners, such as those endogenously produced in the test cell or animal. This may be of particular assistance in examining the function of specific RXR subtype combinations, or even for further studying the potential for Usp—Usp interactions.

The invention herein provides the further advantage that specific heterodimer pairs can be examined by their introduction into the system as a single chimeric protein, e.g., as a fusion protein, rather than by separate introduction of two constructs.

In addition, studies described in the Examples herein indicate that many of the combinations may have unique properties of ligand independence or repression that may have significance to their application for therapeutic purposes. For example, certain of the invention chimeric proteins that transactivate gene expression may be useful as a "gene switch," for modulating expression of an exogenous gene in a mammalian system or in plants, fungi and other non-mammalian species. When the FDs transactivate the response element-containing promoter (e.g., in the presence of ligand), the exogenous gene is switched on; when the FDs repress the promoter, the exogenous gene is switched off.

In nature, dimers of nuclear hormone receptors are unstable and, hence, are not useful in x-ray crystallography studies to determine structure. Because of the demonstrated stability of the invention FD heterodimers, they may be advantageously used in the preparation of crystals for x-ray diffraction studies for use in rational design of ligands to develop new steroids, insecticides, steroid antagonists, and the like, as described hereinbelow. Crystal structure may also permit deduction of the structure of ligands for orphan receptors. It is also contemplated that such crystals of the invention FDs can be used for preparation of antibodies that react with the heterodimers using methods known in the art.

In accordance with another embodiment of the present invention, there are provided isolated protein crystals suitable for x-ray diffraction analysis of a purified invention chimeric protein. In alternative embodiments, the crystal may be obtained of a ligand bound to a purified chimeric protein so as to form a chimeric protein-ligand complex, or a crystal may be obtained of a putative response element bound to purified fusion protein or fusion protein ligand complex as described herein. The invention additionally contemplates a set of x-ray diffraction crystal coordinates obtained by x-ray diffraction of any such invention isolated protein crystals.

A variety of methods are known in the art for purifying proteins and obtaining crystals of the purified proteins, for example growing crystals in microgravity and/or by vapor diffusion (D. R. Davies and D. M. Segal, *Meth. Enzymol.* 22:266, 1971). Crystals of purified proteins can also be obtained commercially. To aid in the purification of the invention fusion proteins, it is recommended to add a His tag to the amino terminus of the fusion protein, as is known in the art and described in Example 6 herein. Addition of such a His tag does not interfere with dimerization of the invention fusion proteins.

In accordance with still another embodiment of the present invention, there are provided methods for identifying potential ligand(s) for member(s) of the steroid/thyroid hormone nuclear receptor superfamily utilizing a set of atomic coordinates obtained by x-ray diffraction analysis of an invention purified protein crystal. The invention assay method comprises creating a three-dimensional structure of a chimeric protein formed into a functional entity (i.e., by dimerization of dimerization domains contained therein) as defined by the atomic coordinates obtained by x-ray diffraction studies, employing the three-dimensional structure to design or select the potential ligand; synthesizing the potential ligand; and then contacting the potential ligand with an invention functional entity in the presence of a response element operatively linked to a marker protein under conditions suitable for causing expression of the marker protein to determine the ability of the potential ligand to transactivate expression of the marker protein. The potential ligand can be designed de novo or designed from a ligand.

Methods for obtaining a set of atomic coordinates of a protein crystal using x-ray diffraction and for creating a three-dimensional model of a protein from such a set of atomic coordinates are known in the art. Such procedures are disclosed, for example, in U.S. Pat. No. 5,856,116, which is incorporated herein by reference in its entirety. For example, x-ray data sets can be collected on a R-axis IIC image plate system and/or on a 2.2.Å Synchrotron data set for refinement of the three-dimensional structure (i.e., the model). Then, the data can be collected at Cornell High Energy Synchrotron Source ("CHESS") on a charge-couple device and reduced to structure factor amplitudes using the Denzo Software Package (Denzo—An Oscillation Data Processing Program For Macro Molecular Crystallography, ©1993, Daniel Gewirth, Yale University). Oscillation photographs can be integrated and reduced to structure factor amplitudes using software supplied by the manufacturer (Molecular Structures Corp., Dallas, Tex.).

Refined heavy atom parameters can be used to compute multiple isomorphous replacement phases. Solvent flattening and phase extension (CCP4-Collaborative Computing Project No. 4, A Suite of Programs for Protein Crystallography; Daresbury Laboratory, Warrington, WA4 4AD, U.K. (1979)) can be used to improve the map and allow identification of some of the residues in the protein core. Cycles of model building (Quanta, version 4.0b, Molecular Simulations Inc., Burlington Mass.), positional refinement, (Brunger, A. T., *J. Acta Cryst.*, A46:46–57, 1990); Brunger, A. T. et al., *J. Acta Cryst.*, A4:585–93, 1990) and phase combination (CCP4-Collaborative Computing Project, supra) can be carried out until the switch to phases calculated from the model can be made. Refinement against −16° C., 2.2.Å data can be continued to allow the more difficult loop regions of the protein to be constructed.

The invention will now be described in greater detail by reference to the following non-limiting examples.

EXAMPLE 1

Design of Ecdysone Receptor-Usp/RXR Functional Dimers

Two classes of chimeric proteins were constructed as fusion proteins to study the activity of EcR-Usp/RXR functional dimers. In one class, EcR is at the N-terminus of a fusion protein, and in the other class the binding partner (either Usp or RXR) is at the N-terminus (FIG. 1). To facilitate formation of the functional dimers and allow for insertion of polypeptide linkers between the receptor and its binding partner in the fusion protein, a 5 amino acid bridge that also encodes the restriction endonuclease site for SfiI was inserted between the two open reading frames (ORFs).

A double stranded SfiI compatible oligonucleotide encoding the amino acid sequence GPGGGSGGGSGT (SEQ ID NO:17) was designed to provide a high degree of predicted flexibility while attempting to minimize repetitive sequence within the oligonucleotide. This nucleotide sequence incorporated the SfiI site at the 5' end of the insert to allow for ease in increasing the number of linker segments within a previously existing construct. By phosphorylating the 36-base-pair double stranded oligonucleotides and ligating them into SfiI digested FD plasmid templates, FDs were produced with peptide linkers of variable length that increased by 12 amino acid increments.

Construction of Fusion Proteins Containing the Ecdysone Receptor.

FIG. 1 shows the schematically fusion protein functional dimer constructs R/U(N)E and E(N)R/U. Construction of the invention fusion proteins began with modification of the N and C termini of human RXRα, dmUsp and dmEcR ORFs subcloned into the cloning vector SK-NBN (pBSK with a modified polylinker). An SfiI site was inserted at either end of each receptor, in-frame, by PCR mutagenesis.

For the hRXR N-terminal SfiI site, the primer in the 5' direction was GTAGAATTCGGCCAACAGGGCCCATG-GACACCAAACATTTC (SEQ ID NO:18); and the primer in the 3' direction was GATGGGGGAGCTCAGGGTGC (SEQ ID NO:19).

For the C-terminal SfiI site, the primer in the 5' direction was GGAGAGCTCGAGGCCTACTGCA (SEQ ID NO:20); and the primer in the 3' direction was ACCATC-GATTCAGGGCCCTGTTGGCCCGTGCGGCGCCTC (SEQ ID NO:21).

For the dmusp N terminal SfiI site, the primer in the 5' direction was GTAGAATTCGGCCAACAGGGCCCATG-GACAACTGCGACCAG (SEQ ID NO:22); and the primer in the 3' direction was CAGCACGTGGACCATTGACA (SEQ ID NO:23).

For the C-terminal SfiI site, the primer in the 5' direction was GGAGAGCTCTTTCTCGAGCAGCTG (SEQ ID NO:24); and the primer in the 3' direction was ACCATC-GATTCAGGGCCCTGTTGGCCCCTC-CAGTTTCATCGCCA GGCCG (SEQ ID NO:25).

For the ecdysone receptor N-terminal SfiI site, VP16 sequences were fused in frame to the NcoI site approximately 200 base pairs into the ecdysone receptor ORF, creating an SfiI site at the VP16-ecdysone receptor boundary.

For the VP 16 insertion site, the primer in the 5' direction was CATAAGCTTATGGGACAGACACTGATGG- GACGGCCC (SEQ ID NO:26) and the primer in the 3' direction was CAGAGACCATGGGCCCTGTTGGC-CCCCCACC (SEQ ID NO:27).

For the ecdysone receptor C-terminus insertion site, the primer in the 5' direction was TTACCGCTAGCTCCACCA (SEQ ID NO:28); and the primer in the 3' direction was GTAGATATCAGGGCCCTGTTGGC-CCAGTCGTCGAGT (SEQ ID NO:29). All primer sequences are written 5' to 3'.

For VP16 (S. J. Triezenberg et al., *Genes Dev.*, 2:718–729, 1988) fusion to RXR and Usp, the VP16 sequence region was removed from VE using the SfiI site at the 3' boundary of VP16 sequence for fusion of the 260 base pair VP16 fragment into the N-terminal compatible SfiI site of previously modified RXR and Usp ORFs. All fusion receptor variants were originally produced by insertion of both ORFs at the central SfiI site. Linker segments with SfiI compatible overhangs were produced by annealing two linker-encoding oligonucleotides having the sequence GGGCCAGGAG-GTGGCTCCGGGGGAGGTTCAGGCACA (SEQ ID NO:30) in the 5' direction, and the sequence GCCTGAAC-CTCCCCCGGAGCCACCTCCTGGCCCTGT (SEQ ID NO:31) in the 3' direction.

EcR F-domain deletion constructs were produced by inserting an in-frame polylinker upstream of the SfiI-N-terminal modified RXR for reception of compatible F-domain deleted ecdysone receptor fragments. The polylinker in the 5' direction, AAGCTTGAGAGATCTGGGACGGCGC-CCCCGGGGCTAGCGGGCCAACA (SEQ ID NO:32) encoded (from Bgl II) the peptide sequence IWDGAPGAS (SEQ ID NO:33) and restriction sites Hind III-Bgl II-Nar I-Sma I-Nhe I with an SfiI compatible 3' end. Hind III-Bgl II, Hind III-Nar I, etc. fragments of the ecdysone receptor were inserted into this polylinker for fusion of F-domain deletions to RXR. FIG. 2B shows schematically the F-domain deletion constructs of E0R made by this procedure.

PCR reactions for production of receptor mutants were performed using 100 ng plasmid template, 500 ng of each primer, and reaction conditions outlined by the manufacturer for Pwo (Boerhinger Mannheim) high-fidelity polymerase. A program of 1 min. 94° C./1 min. 45° C./1 min. 72° C./1 min. for 20 cycles was used for production of all PCR products used. For constructs containing multiple repeat linker segments, fusion receptors were linearized by SfiI digest, and linker segment oligonucleotides, kinased to allow multiple tandem insertions, were ligated into the site by standard methods. Inserted linker segment repeats of between 0 and 5 linker segments were found by restriction endonuclease digest followed by sizing on 3% agarose gels. For the studies reported here, the minimum linker length contained only the 5 amino acid fusion bridge (signified herein by linker segment designation "0") and the maximum was 245 amino acids (including a five amino acid fusion bridge) (signified herein by linker segment designation "20").

Plasmids from clones of interest were prepared on a large scale for use in transfection and other analysis including confirmatory sequencing of constructs. All receptors were subcloned into vector LNCX (A. D. Miller, GenBank Acc. No. M28247) (with an extended polylinker) for use in transfection.

EXAMPLE 2

Transfection of FD Constructs

For quantitative transactivation analysis, transfections were performed in triplicate in 24-well plates by calcium-phosphate co-precipitation with 100 ng of an individual receptor, the reporter plasmid E4-luc, and pCH110 (SV40-β-galactosidase) as an internal control. Briefly, the reporter plasmid, E4-luc, was constructed of 4-tandem EcREs inserted upstream of a thymidine kinase gene minimal promoter directing luciferase expression. EcRE oligonucleotides were as described by Thomas et al., supra (1993) with BamHI/BglII compatible ends. 1 µM ligand was added at the time of transfection, and the cells were harvested for luciferase assay 40 hours later. Harvested cell extracts were split, and one part was analyzed in a luminometer for luciferase activity and the other part was analyzed for β-galactosidase activity using an orthonitrophenyl galactoside assay by standard methods. Luciferase levels were normalized to β-galactosidase values to correct for slight differences in transfection efficiency.

Preparation of the invention fusion protein FDs for gel shift analysis by transient transfection into 293 cells was as follows: 300 ng of individual receptor plasmids and 100 ng pCH110 internal control plasmid were cotransfected into 293 cells at 60% density in Costar 6-well plates. One well of each group was treated with 1 µM murA as ligand at the time of transfection. 40 hours later, extracts of transfected 293 cells were made by scraping the cells from a well into a low volume of phosphate buffered saline, pelleting the cells, resuspending them in 200 µl 5×gel shift buffer (Yao et al., supra 1992), and sonicating with a Kontes cell disrupter for three 10-sec. bursts at output level 30. The extracts were then centrifuged to clear the lysate and the protein was quantified. Extract volumes were adjusted with buffer to a concentration of 1 mg/ml and frozen at −70° C. until use. β-galactosidase activity was assayed as above to determine relative transfection efficiency of each well.

EXAMPLE 3

Gel Mobility Shift Analysis

Comparative gel mobility shift analyses of FDs with control in vitro translated receptor complexes were performed using double stranded EcRE probes and labeled by Klenow fill using $^{32}$P-dCTP and cold dGAT by standard methods. In vitro translated proteins used as controls were produced using the T3/T7 TNT (Promega) transcription/translation system following the manufacturer's protocol. In vitro translated proteins were qualitatively examined by 5% SDS-PAGE using protocols as described (J. Sambrook et al. *Molecular Cloning: A Laboratory Manual*, Cold Spring Harbor Press, Cold Spring Harbor, N.Y., 1989) to ensure the presence of full-length products of the proper molecular weight. Reaction conditions for protein-probe interaction and gel electrophoresis were essentially identical to those disclosed in Yao et al., supra 1992. However, to improve comparison between samples, reaction mixtures (including dimer partners and probe) were prepared as a cocktail and distributed equally to individual tubes with receptor proteins. β-galactosidase assay indicated that all samples were essentially equivalent, so equal volumes (10 µl) of extract were used in each reaction in a final reaction volume of 30 µl. The reactions were allowed to proceed at 23° C. for 5 minutes at which time ligand or vehicle was added and the reaction allowed to continue for 20 additional minutes. Band volumes were quantified using laser scanning densitometry.

Western Blot Analysis 6-well plates of 293 cells transfected with 2 µg of receptor construct and 100 ng of pCH110 were harvested in PBS and lysed by three rounds of freezing and thawing. β-galactosidase assay of lysates indicated equivalent transfection efficiency for all constructs so equivalent protein (7.5 µg) was loaded and run on a 12.5% SDS-PAGE gel and transferred to nitrocellulose by standard methods (Sambrook et al., supra 1989). The transferred filter was incubated with the anti-EcR monoclonal antibody DDA2.7 (Koelle et al., supra 1991) at a 1/1000 dilution at 4° C. for 48 hours. After washes, anti-mouse IgG (1/5000) was added for 1 hour, washed away, and the blot processed for chemiluminescence and exposed to film.

An autoradiogram of FDs and controls treated either with control vehicle or with 1 μM of murA as ligand was made with markers indicating endodimer FD or wild type receptor-binding complex band shifts. E+U and E+R were control lanes of in vitro translated proteins for sizing of endodimer band shifts. FIG. 2A is a graph that quantifies endodimer-sized band volumes obtained from the autoradiogram.

A prominent band co-migrating with band shifts for the separate dimer complexes (E+U and E+R) was observed in many lanes and indicated that some of the FDs formed functional DNA-binding internal dimers that we designate "endodimers." U0E displayed a barely detectable endodimer band that was perceptibly increased (2-fold) in intensity by the presence of ligand (FIG. 2B). The addition of 5 linker segments in U5E appeared to amplify the overall intensity of the shift, but still displayed minimal response to ligand. UNE constructs displayed faint bands above the weak endodimer band-shift that were equally as intense. These bands were occasionally visible but were proportionally less intense than the endodimer band shift of other FDs described below. R0E, which is analogous to U0E but with substitution of U for R, formed a clear endodimer band that was increased 4-fold by ligand (FIG. 2B), and unequivocally demonstrated FD responds to hormone. R5E, with a longer linker, had slightly decreased basal, and slightly increased ligand-stimulated, EcRE binding (5-fold) compared to R0E. The higher molecular weight shift bands observed in UNE lanes were not visible in ligand-treated R5E lanes (FIG. 2A).

ENU constructs indicated that FDs in which E was positioned at the N-terminus formed endodimers and bound the EcRE probe an average of 10 times better than UNE constructs. ENU constructs bound probe 80–150% more readily than even other FDs with high-level EcRE binding (i.e., E5R, discussed below), but displayed nearly complete insensitivity to ligand for formation of DNA-binding complexes. Like UNE FDs, the longer linker length of E5U did not significantly increase the binding to EcRE or responsiveness to murA, relative to E0U (FIGS. 2A and 2B). ENR constructs, like ENUs, also demonstrated a greater affinity for the probe than the reversed constructs (FIG. 2A). Unlike ENU constructs, ENR FDs had a high degree of ligand dependence for endodimer formation. E5R displayed a slightly decreased shift from the rate of basal transcription, and a slightly elevated ligand-stimulated shift (11-fold relative induction) in comparison to E0R (7-fold), much like R0E and R5E. Non-transfected cells, or cells transfected only with E, displayed no detectable shift even after prolonged exposure. At concentrations of protein higher than those used in these gel-shift reactions, a shift of E in combination with endogenous RXR was observed. Separate experiments also confirmed that FDs specifically bound EcREs and not unrelated control probes that included thyroid hormone response elements.

FIG. 3 shows relative luciferase expression of FD constructs with or without 1 μM murA. The results of these studies are summarized in Table 1 below and show repression of monomeric receptors and monomeric dimer partners by E0U and U0E FDs.

TABLE 1

|  | U0E | R0E | U5E | R5E | E0U | E0R | E5U | E5R | E | E + U |
|---|---|---|---|---|---|---|---|---|---|---|
| −Lig/E$_4$ | 0.75 | 0.18 | 0.52 | 0.25 | 0.17 | 0.21 | 0.41 | 0.46 | 1.08 | 1.74 |
| +Lig/E$_4$ | 0.55 | 1.75 | 0.69 | 1.50 | 0.40 | 3.39 | 0.62 | 3.89 | 7.72 | 8.34 |
| Rel. Ind. | 0.7 | 9.7 | 2.7 | 6.0 | 2.4 | 16.2 | 1.6 | 8.4 | 7.1 | 4.8 |

−Lig/E$_4$ = luciferase activity in cells transiently co-transfected with FDs and monomeric receptors vs. reporter only without ligand
+Lig/E$_4$ = luciferase activity in cells transiently co-transfected with FDs and monomeric receptors vs. reporter only with ligand
Rel. Ind. = relative induction of individual receptor groups As shown in Table 1, UNE and ENU constructs either did not stimulate luciferase expression or appeared to actually function as repressors of basal transcription. E0U in the absence of ligand, for instance, reduced E4-luc transcription to only 17% of the basal expression level. RNE and ENR constructs, by comparison, functioned much more like separate E+R, although both the basal and induced levels were proportionally decreased relative to the monomeric receptors. As might be predicted from the mobility shift experiments, E5R provided the closest profile to the monomeric (i.e., wild type) separate receptors, having approximately 50% of the E+R induced expression level. By contrast, both E0R and E5R, however, had greater relative inductions than separate E+R (16.2- and 8.4-fold, respectively, versus 7.1-fold).

EXAMPLE 4

Figure 4A:
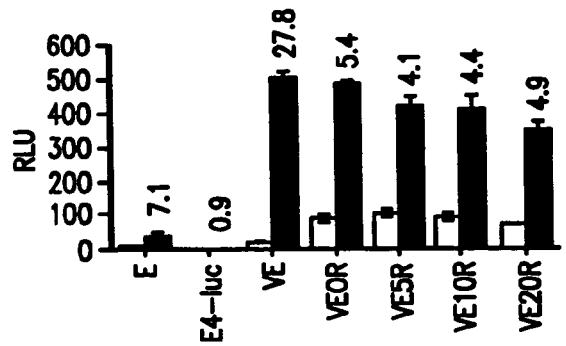
FIGS. 4A–B are two graphs illustrating the results of transient transfection assays conducted using either VP16-fused monomeric receptors or invention fusion protein FDs with increasing linker lengths.
Figure 4B:
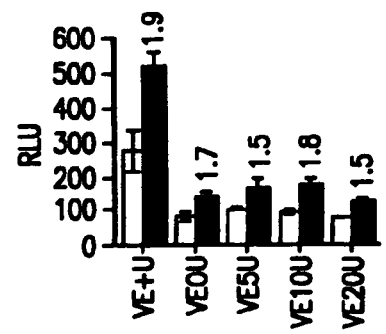

Addition of the potent VP 16 transactivation (τ) domain to the N-terminus of FD constructs was used to further examine transactivation by FDs. To test the possibility that distortion of the endodimer by a short linker (0 linker segments) contributed to inhibited transactivation, the number of linker segments in the linker between the units in the invention fusion proteins was expanded to a maximum of 20 linker segments for ENR and ENU variants. As shown in FIG. 4A, addition of a VP 16 τ domain to either the E monomer (VE) or to FDs (VENR or VENU) resulted in a 12 to 15-fold overall increase in luciferase expression. These VENR FDs containing linkers of variable length produce a stimulated level of transcription virtually identical to separate VE protein, suggesting that augmentation of ENR proteins with VP16 τ domain compensated for any loss in transactivation resulting from the fusion of the receptor and dimer partner into the invention fusion proteins. Notably, however, the level of basal, induced expression was increased 7 to 8-fold over monomeric receptors. This resulted in a dramatic decrease in the relative fold induction, from 27.8-fold for separate VE to 4.1 to 5.4-fold for FDs (FIG. 4A). In addition, the increase from a 5 amino acid linker to a 245 amino acid linker had little effect on either basal or activated VENR transactivation with the exception of a subtle decrease in both levels in the FDs having the longer 125 (10 linker segments) and 245 amino acid (20 linker segment) linkers. As shown in FIG. 4B, VENU constructs displayed neither the basal nor induced level of expression of separate VE+U, even though the overall level of transactivation was significantly increased relative to E+U complexes without a heterologous transactivating domain. Like the VENR proteins, the addition of increased linker segments to the VENU constructs had a minimal effect on basal or induced transcriptional activation.

EXAMPLE 5

Figure 6:
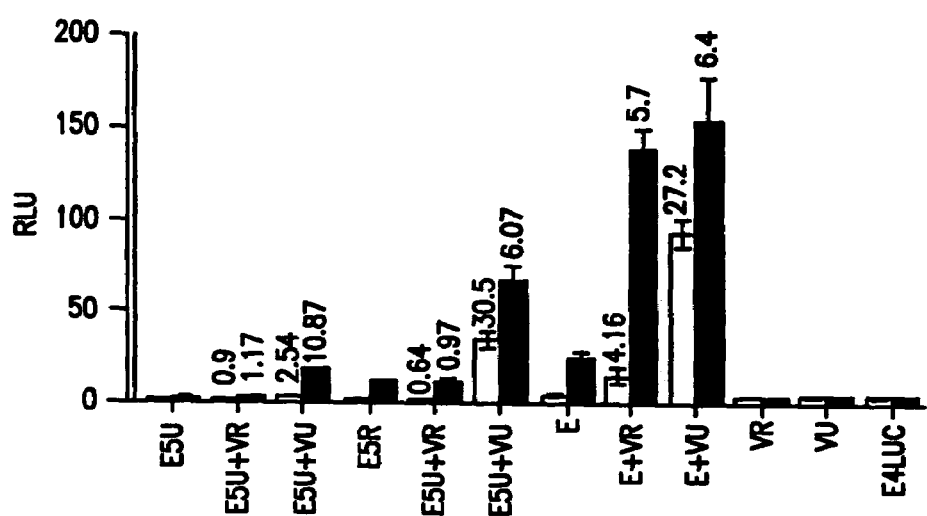
FIG. 6 is a graph showing a comparison of results (in RLU) obtained in assays in which E5U and E5R compete with monomeric VRXR (VR) or monomeric VUsp (VU) in the presence of vehicle only (open bars, i.e., −MurA) or murA as ligand (black bars, i.e., +MurA). FDs and receptor combinations are labeled along the abscissa. Numbers above the bars represent the fold-increase relative to FD or receptor without addition of VR or VU. E4LUC at the extreme right is reporter plasmid alone as control.

To elucidate the propensity of fusion protein partners to dimerize with each other over other monomeric suitable dimer partners, the influence of monomeric dimer partners on FD transactivation properties was assayed. In the transient transfection experiments shown in FIG. 6, R and U proteins with N-terminal VP16 fusions (VR and VU, respectively) were utilized to probe E5U and E5R promiscuity. E5R and E5U constructs were used because previous experiments suggested that they displayed properties that were the most similar to monomeric (i.e., wild type) receptors. When both E5R and E5U constructs were cotransfected into 293 cells in equimolar quantities along with the E4-luc reporter, VR cotransfection was not observed to significantly influence either E5U or E5R function, even though VR was found to augment E-mediated transactivation alone by >5-fold either with or without ligand (FIG. 6). VU, on the other hand, delectably interacted with E5R, and to a lesser extent with E5U. Ligand-dependent transactivation was observed for E5U+VUsp at approximately 10% of the ligand-stimulated level of VUsp with E, whereas E5R+VUsp activated to nearly 50% of the VUsp+E level. VR and VU alone had no influence on E4-luc expression either with or without murA.

EXAMPLE 6

Using a modification of the method for constructing invention fusion proteins described above in Example 1, fusion proteins were constructed having a *Bombyx* ecdysone receptor (BEcR) in the amino terminal half of the fusion protein, a linker bridge of 5 amino acids, and either RXR (BE0R) or Usp (BE0U) as the dimer partner placed at the C-terminal half of the fusion protein. To facilitate cloning, the BEcR amino acid sequence in each of these fusion proteins was augmented at the C-terminal end with amino acids 650–878 from the *Drosophila melanogaster* ecdysone receptor. Similar constructs were made wherein a His tag was positioned at the amino terminus of the fusion protein to facilitate purification of the fusion protein (HisBE0R and HisBE0U, respectively).

Gel mobility shift assays using tebufenozide and MurA as ligand were conducted as described in Example 3 above to determine whether functional dimers formed from the BE0R and BE0U fusion proteins. The results of these assays showed the both BE0R and BE0U dimerize and constitutively bind target DNA irrespective of the presence of ligand. When the study was repeated using HisDE0R, HisBE0R and HisBE0U, it was determined that the His tag does not effect the ability of these fusion proteins to bind target DNA.

It will be apparent to those skilled in the art that various changes may be made in the invention without departing from the spirit and scope thereof, and therefore, the invention encompasses embodiments in addition to those specifically disclosed in the specification.

What is claimed is:

1. A chimeric protein comprising a fusion of at least two functional protein units,
    wherein each functional protein unit comprises a ligand binding domain, an optional hinge domain a DNA binding domain, and a dimerization domain of a member of the steroid/thyroid hormone nuclear receptor superfamily;
    wherein said at least two functional protein units are covalently fused into a single polypeptide molecule by (i) fusion of said protein units, or (ii) use of a linker interposed between said protein units;
    wherein at least one functional protein unit is selected from the group consisting of the retinoid X receptor and the ultraspiracle protein;
    wherein the other functional protein unit is selected from the group consisting of ecdysone receptors, Vitamin D3 receptors, retinoic acid receptors, peroxisome proliferator-activated receptors, thyroid hormone receptors, steroid and xenobiotic receptors, farnesoid X receptors, and liver X receptors; and
    wherein said chimeric protein is capable of at least one function selected from the group consisting of DNA binding, ligand binding, transactivation and dimerization.

2. The chimeric protein according to claim 1 wherein said chimeric protein forms an endodimer.

3. The chimeric protein according to claim 1 wherein at least one functional protein unit is non-mammalian.

4. The chimeric protein according to claim 3 wherein the at least one functional protein unit is from an insect species.

5. The chimeric protein according to claim 1 wherein at least one functional protein unit comprises an ecdysone receptor.

6. The chimeric protein according to claim 5 wherein the ecdysone receptor comprises a *Drosophila* ecdysone receptor.

7. The chimeric protein according to claim 5 wherein the ecdysone receptor comprises a *Lepidoptera* ecdysone receptor.

8. The chimeric protein according to claim 5 wherein the ecdysone receptor comprises a *Bombyx* ecdysone receptor.

9. The chimeric protein according to claim 3 wherein at least one functional protein unit comprises the ultraspiracle protein.

10. The chimeric protein according to claim 1 wherein at least one functional protein unit comprises the retinoid X receptor.

11. The chimeric protein according to claim 1 wherein the steroid and xenobiotic receptor functional protein units are selected from the group consisting of SXR, PXR, and BXR.

12. The chimeric protein according to claim 1 wherein the linker contains from about 5 to about 245 amino acids.

13. The chimeric protein according to claim 12 wherein the linker contains from about 53 to about 125 amino acids.

14. The chimeric protein according to claim 12 wherein the linker comprises one or more amino acid residues selected from the group consisting of glycine, proline, serine, alanine and threonine.

15. The chimeric protein according to claim 12 wherein the linker comprises the amino acid sequence of SEQ ID NO:15.

16. The chimeric protein according to claim 1 wherein one or more protein units further comprise a C-terminal domain.

17. The chimeric protein according to claim 1 wherein the DNA binding domains of one or more protein units comprise 66 to 68 amino acids, including 9 cysteines.

18. The chimeric protein according to claim 1 wherein the hinge domain of one or more protein units is the *Bombyx* hinge domain.

19. The chimeric protein according to claim 1 wherein one or more protein units further comprise an activation domain.

* * * * *

SEQUENCE LISTING

```
<160> NUMBER OF SEQ ID NOS: 80

<210> SEQ ID NO 1
<211> LENGTH: 67
<212> TYPE: PRT
<213> ORGANISM: Artificial Sequence
<220> FEATURE:
<223> OTHER INFORMATION: Description of Artificial Sequence: Synthetic
      binding domain of the steroid/thyroid hormone superfamily
      of receptor
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (5)..(6)
<223> OTHER INFORMATION: Variable amino acid
<220> FEATURE:
<221> NAME/KEY: MOD_RES
<222> LOCATION: (8)
<223> OTHER INFORMATION: Variable amino acid
<220> FEATURE:
<221> NAME/KEY: MOD_RES
<222> LOCATION: (10)
<223> OTHER INFORMATION: Variable amino acid
<220> FEATURE:
<221> NAME/KEY: MOD_RES
<222> LOCATION: (12)
<223> OTHER INFORMATION: Variable amino acid
<220> FEATURE:
```

```
<221> NAME/KEY: MOD_RES
<222> LOCATION: (14)..(17)
<223> OTHER INFORMATION: Variable amino acid
<220> FEATURE:
<221> NAME/KEY: MOD_RES
<222> LOCATION: (19)..(20)
<223> OTHER INFORMATION: Variable amino acid
<220> FEATURE:
<221> NAME/KEY: MOD_RES
<222> LOCATION: (23)
<223> OTHER INFORMATION: Variable amino acid
<220> FEATURE:
<221> NAME/KEY: MOD_RES
<222> LOCATION: (26)
<223> OTHER INFORMATION: Variable amino acid
<220> FEATURE:
<221> NAME/KEY: MOD_RES
<222> LOCATION: (28)..(34)
<223> OTHER INFORMATION: Variable amino acid
<220> FEATURE:
<221> NAME/KEY: MOD_RES
<222> LOCATION: (36)..(43)
<223> OTHER INFORMATION: Variable amino acid
<220> FEATURE:
<221> NAME/KEY: MOD_RES
<222> LOCATION: (45)..(47)
<223> OTHER INFORMATION: Variable amino acid
<220> FEATURE:
<221> NAME/KEY: MOD_RES
<222> LOCATION: (49)..(50)
<223> OTHER INFORMATION: Variable amino acid
<220> FEATURE:
<221> NAME/KEY: MOD_RES
<222> LOCATION: (52)..(53)
<223> OTHER INFORMATION: Variable amino acid
<220> FEATURE:
<221> NAME/KEY: MOD_RES
<222> LOCATION: (55)..(56)
<223> OTHER INFORMATION: Variable amino acid
<220> FEATURE:
<221> NAME/KEY: MOD_RES
<222> LOCATION: (59)..(60)
<223> OTHER INFORMATION: Variable amino acid
<220> FEATURE:
<221> NAME/KEY: MOD_RES
<222> LOCATION: (63)..(65)
<223> OTHER INFORMATION: Variable amino acid

<400> SEQUENCE: 1

Cys Xaa Xaa Cys Xaa Xaa Asp Xaa Ala Xaa Gly Xaa Tyr Xaa Xaa Xaa
 1               5                  10                  15

Xaa Cys Xaa Xaa Cys Lys Xaa Phe Phe Xaa Arg Xaa Xaa Xaa Xaa
            20                  25                  30

Xaa Xaa Cys Xaa Xaa Xaa Xaa Xaa Xaa Xaa Cys Xaa Xaa Xaa Lys
        35                  40                  45

Xaa Xaa Arg Xaa Xaa Cys Xaa Xaa Cys Arg Xaa Xaa Lys Cys Xaa Xaa
    50                  55                  60

Xaa Gly Met
65

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 2

Gly Gly Gly Gly Ser
 1               5
```

```
<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 3

Gly Gly Gly Gly Ser Gly Gly Gly Gly Ser
 1               5                  10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 4

Gly Lys Ser Ser Gly Ser Gly Ser Glu Ser Lys Ser
 1               5                  10

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 5

Gly Ser Thr Ser Gly Ser Gly Lys Ser Ser Glu Gly Lys Gly
 1               5                  10

<210> SEQ ID NO 6
<211> LENGTH: 18
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 6

Gly Ser Thr Ser Gly Ser Gly Lys Ser Ser Glu Gly Ser Gly Ser Thr
 1               5                  10                  15

Lys Gly

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 7

Gly Ser Thr Ser Gly Ser Gly Lys Ser Ser Glu Gly Lys Gly
 1               5                  10

<210> SEQ ID NO 8
<211> LENGTH: 18
<212> TYPE: PRT
<213> ORGANISM: Artificial Sequence
<220> FEATURE:
<223> OTHER INFORMATION: Description of Artificial Sequence: Chimeric
```

-continued

```
            protein linker

<400> SEQUENCE: 8

Gly Ser Thr Ser Gly Ser Gly Lys Pro Gly Ser Gly Glu Gly Ser Thr
1               5                   10                  15

Lys Gly

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 9

Glu Gly Lys Ser Ser Gly Ser Gly Ser Glu Ser Lys Glu Phe
1               5                   10

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 10

Ser Arg Ser Ser Gly
1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 11

Ser Gly Ser Ser Cys
1               5

<210> SEQ ID NO 12
<211> LENGTH: 28
<212> TYPE: PRT
<213> ORGANISM: Artificial Sequence
<220> FEATURE:
<223> OTHER INFORMATION: Description of Artificial Sequence: Trypsin
      sensitive linker

<400> SEQUENCE: 12

Ala Met Gly Arg Ser Gly Gly Gly Cys Ala Gly Asn Arg Val Gly Ser
1               5                   10                  15

Ser Leu Ser Cys Gly Gly Leu Asn Leu Gln Ala Met
            20                  25

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 13
```

```
Ala Met Gly Gly Ser Ala Met
  1               5
```

<210> SEQ ID NO 14
<211> LENGTH: 13
<212> TYPE: DNA
<213> ORGANISM: Artificial Sequence
<220> FEATURE:
<223> OTHER INFORMATION: Description of Artificial Sequence: Nucleotide
      encoding SfiI recognition site
<220> FEATURE:
<221> NAME/KEY: modified_base
<222> LOCATION: (5)..(9)
<223> OTHER INFORMATION: a, t, c or g

<400> SEQUENCE: 14
ggccnnnnng gcc                                                           13

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 15

```
Gly Pro Gly Gly Gly Ser Gly Gly Gly Ser Gly Thr
  1               5                  10
```

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: GAL4
      response element

<400> SEQUENCE: 16

```
Cys Gly Gly Ala Gly Gly Ala Cys Thr Gly Thr Cys Cys Thr Cys Cys
  1               5                  10                  15
Gly
```

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: SfiI
      compatible oligonucleotide

<400> SEQUENCE: 17

```
Gly Pro Gly Gly Gly Ser Gly Gly Gly Ser Gly Thr
  1               5                  10
```

<210> SEQ ID NO 18
<211> LENGTH: 41
<212> TYPE: DNA
<213> ORGANISM: Artificial Sequence
<220> FEATURE:
<223> OTHER INFORMATION: Description of Artificial Sequence: hRXR
      N-terminal SfiI primer 5'

<400> SEQUENCE: 18
gtagaattcg gccaacaggg cccatggaca ccaaacattt c                            41

<210> SEQ ID NO 19

```
<211> LENGTH: 20
<212> TYPE: DNA
<213> ORGANISM: Artificial Sequence
<220> FEATURE:
<223> OTHER INFORMATION: Description of Artificial Sequence: hRXR
      N-terminal SfiI primer 3'

<400> SEQUENCE: 19 gatggggag ctcagggtgc                                              20

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: hRXR
      N-terminal SfiI primer 5'

<400> SEQUENCE: 20
ggagagctcg aggcctactg ca                                          22

<210> SEQ ID NO 21
<211> LENGTH: 39
<212> TYPE: DNA
<213> ORGANISM: Artificial Sequence
<220> FEATURE:
<223> OTHER INFORMATION: Description of Artificial Sequence: hRXR
      N-terminal SfiI primer 3'

<400> SEQUENCE: 21
accatcgatt cagggccctg ttggcccgtg cggcgcctc                        39

<210> SEQ ID NO 22
<211> LENGTH: 41
<212> TYPE: DNA
<213> ORGANISM: Artificial Sequence
<220> FEATURE:
<223> OTHER INFORMATION: Description of Artificial Sequence: dmusp
      N-terminal SfiI primer 5'

<400> SEQUENCE: 22
gtagaattcg gccaacaggg cccatggaca actgcgacca g                     41

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: dmusp
      N-terminal SfiI primer 3'

<400> SEQUENCE: 23
cagcacgtgg accattgaca                                             20

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: dmusp
      N-terminal SfiI primer 5'

<400> SEQUENCE: 24
ggagagctct ttctcgagca gctg                                        24

<210> SEQ ID NO 25
<211> LENGTH: 49
```

```
<212> TYPE: DNA
<213> ORGANISM: Artificial Sequence
<220> FEATURE:
<223> OTHER INFORMATION: Description of Artificial Sequence: dmusp
      N-terminal SfiI primer 3'

<400> SEQUENCE: 25
accatcgatt cagggccctg ttggcccctc cagtttcatc gccaggccg          49

<210> SEQ ID NO 26
<211> LENGTH: 36
<212> TYPE: DNA
<213> ORGANISM: Artificial Sequence
<220> FEATURE:
<223> OTHER INFORMATION: Description of Artificial Sequence: VP16
      N-terminal SfiI primer 5'

<400> SEQUENCE: 26
cataagctta tgggacagac actgatggga cggccc                       36

<210> SEQ ID NO 27
<211> LENGTH: 31
<212> TYPE: DNA
<213> ORGANISM: Artificial Sequence
<220> FEATURE:
<223> OTHER INFORMATION: Description of Artificial Sequence: VP16
      N-terminal SfiI primer 3'

<400> SEQUENCE: 27
cagagaccat gggccctgtt ggccccccac c                            31

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: VP16
      C-terminal SfiI primer 5'

<400> SEQUENCE: 28
ttaccgctag ctccacca                                           18

<210> SEQ ID NO 29
<211> LENGTH: 36
<212> TYPE: DNA
<213> ORGANISM: Artificial Sequence
<220> FEATURE:
<223> OTHER INFORMATION: Description of Artificial Sequence: VP16
      C-terminal SfiI primer 3'

<400> SEQUENCE: 29
gtagatatca gggccctgtt ggcccagtcg tcgagt                       36

<210> SEQ ID NO 30
<211> LENGTH: 36
<212> TYPE: DNA
<213> ORGANISM: Artificial Sequence
<220> FEATURE:
<223> OTHER INFORMATION: Description of Artificial Sequence: Annealing
      two linker encoding oligonucleotides 5'

<400> SEQUENCE: 30
gggccaggag gtggctccgg gggaggttca ggcaca                       36

<210> SEQ ID NO 31
<211> LENGTH: 36
<212> TYPE: DNA
```

```
<213> ORGANISM: Artificial Sequence
<220> FEATURE:
<223> OTHER INFORMATION: Description of Artificial Sequence: Annealing
      two linker encoding oligonucleotides 3'

<400> SEQUENCE: 31
gcctgaacct cccccggagc cacctcctgg ccctgt                              36

<210> SEQ ID NO 32
<211> LENGTH: 47
<212> TYPE: DNA
<213> ORGANISM: Artificial Sequence
<220> FEATURE:
<223> OTHER INFORMATION: Description of Artificial Sequence: F-domain
      deleted ecdysone receptor fragment polylinker 5'

<400> SEQUENCE: 32
aagcttgaga gatctgggac ggcgcccccg gggctagcgg gccaaca                  47

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Bgl II
      peptide sequence

<400> SEQUENCE: 33

Ile Trp Asp Gly Ala Pro Gly Ala Ser
  1               5

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 34

Ala Met Gly Gly Ser Gly Gly Ser Ala Met
  1               5                  10

<210> SEQ ID NO 35
<211> LENGTH: 13
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 35

Ala Met Gly Gly Ser Gly Gly Ser Gly Gly Ser Ala Met
  1               5                  10

<210> SEQ ID NO 36
<211> LENGTH: 16
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 36

Ala Met Gly Gly Ser Gly Gly Ser Gly Gly Ser Gly Gly Ser Ala Met
  1               5                  10                  15
```

-continued

```
<210> SEQ ID NO 37
<211> LENGTH: 19
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 37

Ala Met Gly Gly Ser Gly Gly Ser Gly Gly Ser Gly Gly Ser Gly Gly
 1               5                  10                  15

Ser Ala Met

<210> SEQ ID NO 38
<211> LENGTH: 22
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 38

Ala Met Gly Gly Ser Gly Gly Ser Gly Gly Ser Gly Gly Ser Gly Gly
 1               5                  10                  15

Ser Gly Gly Ser Ala Met
            20

<210> SEQ ID NO 39
<211> LENGTH: 25
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 39

Ala Met Gly Gly Ser Gly Gly Ser Gly Gly Ser Gly Gly Ser Gly Gly
 1               5                  10                  15

Ser Gly Gly Ser Gly Gly Ser Ala Met
            20                  25

<210> SEQ ID NO 40
<211> LENGTH: 28
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 40

Ala Met Gly Gly Ser Gly Gly Ser Gly Gly Ser Gly Gly Ser Gly Gly
 1               5                  10                  15

Ser Gly Gly Ser Gly Gly Ser Gly Gly Ser Ala Met
            20                  25

<210> SEQ ID NO 41
<211> LENGTH: 31
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 41

Ala Met Gly Gly Ser Gly Gly Ser Gly Gly Ser Gly Gly Ser Gly Gly
 1               5                  10                  15
```

Ser Gly Gly Ser Gly Gly Ser Gly Gly Ser Gly Gly Ser Ala Met
            20                  25                  30

<210> SEQ ID NO 42
<211> LENGTH: 34
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 42

Ala Met Gly Gly Ser Gly Gly Ser Gly Gly Ser Gly Gly Ser Gly Gly
 1               5                  10                  15

Ser Gly Gly Ser Gly Gly Ser Gly Gly Ser Gly Gly Ser Gly Gly Ser
            20                  25                  30

Ala Met

<210> SEQ ID NO 43
<211> LENGTH: 37
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 43

Ala Met Gly Gly Ser Gly Gly Ser Gly Gly Ser Gly Gly Ser Gly Gly
 1               5                  10                  15

Ser Gly Gly Ser Gly Gly Ser Gly Gly Ser Gly Gly Ser Gly Gly Ser
            20                  25                  30

Gly Gly Ser Ala Met
            35

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 44

Ala Met Gly Gly Gly Ser Ala Met
 1               5

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 45

Ala Met Gly Gly Gly Ser Gly Gly Gly Ser Ala Met
 1               5                  10

<210> SEQ ID NO 46
<211> LENGTH: 16
<212> TYPE: PRT
<213> ORGANISM: Artificial Sequence
<220> FEATURE:
<223> OTHER INFORMATION: Description of Artificial Sequence: Chimeric
      protein linker

```
<400> SEQUENCE: 46

Ala Met Gly Gly Gly Ser Gly Gly Gly Ser Gly Gly Gly Ser Ala Met
1               5                   10                  15

<210> SEQ ID NO 47
<211> LENGTH: 20
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 47

Ala Met Gly Gly Gly Ser Gly Gly Gly Ser Gly Gly Gly Ser Gly Gly
1               5                   10                  15

Gly Ser Ala Met
            20

<210> SEQ ID NO 48
<211> LENGTH: 24
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 48

Ala Met Gly Gly Gly Ser Gly Gly Gly Ser Gly Gly Gly Ser Gly Gly
1               5                   10                  15

Gly Ser Gly Gly Gly Ser Ala Met
            20

<210> SEQ ID NO 49
<211> LENGTH: 28
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 49

Ala Met Gly Gly Gly Ser Gly Gly Gly Ser Gly Gly Gly Ser Gly Gly
1               5                   10                  15

Gly Ser Gly Gly Gly Ser Gly Gly Gly Ser Ala Met
            20                  25

<210> SEQ ID NO 50
<211> LENGTH: 32
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 50

Ala Met Gly Gly Gly Ser Gly Gly Gly Ser Gly Gly Gly Ser Gly Gly
1               5                   10                  15

Gly Ser Gly Gly Gly Ser Gly Gly Gly Ser Gly Gly Gly Ser Ala Met
            20                  25                  30

<210> SEQ ID NO 51
<211> LENGTH: 36
<212> TYPE: PRT
<213> ORGANISM: Artificial Sequence
```

```
<220> FEATURE:
<223> OTHER INFORMATION: Description of Artificial Sequence: Chimeric
      protein linker

<400> SEQUENCE: 51

Ala Met Gly Gly Gly Ser Gly Gly Gly Ser Gly Gly Gly Ser Gly Gly
  1               5                  10                  15

Gly Ser Gly Gly Gly Ser Gly Gly Gly Ser Gly Gly Gly Ser Gly Gly
             20                  25                  30

Gly Ser Ala Met
         35

<210> SEQ ID NO 52
<211> LENGTH: 40
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 52

Ala Met Gly Gly Gly Ser Gly Gly Gly Ser Gly Gly Gly Ser Gly Gly
  1               5                  10                  15

Gly Ser Gly Gly Gly Ser Gly Gly Gly Ser Gly Gly Gly Ser Gly Gly
             20                  25                  30

Gly Ser Gly Gly Gly Ser Ala Met
         35                  40

<210> SEQ ID NO 53
<211> LENGTH: 44
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 53

Ala Met Gly Gly Gly Ser Gly Gly Gly Ser Gly Gly Gly Ser Gly Gly
  1               5                  10                  15

Gly Ser Gly Gly Gly Ser Gly Gly Gly Ser Gly Gly Gly Ser Gly Gly
             20                  25                  30

Gly Ser Gly Gly Gly Ser Gly Gly Gly Ser Ala Met
         35                  40

<210> SEQ ID NO 54
<211> LENGTH: 48
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 54

Ala Met Gly Gly Gly Ser Gly Gly Gly Ser Gly Gly Gly Ser Gly Gly
  1               5                  10                  15

Gly Ser Gly Gly Gly Ser Gly Gly Gly Ser Gly Gly Gly Ser Gly Gly
             20                  25                  30

Gly Ser Gly Gly Gly Ser Gly Gly Gly Ser Gly Gly Gly Ser Ala Met
         35                  40                  45

<210> SEQ ID NO 55
<211> LENGTH: 9
<212> TYPE: PRT
```

```
<213> ORGANISM: Artificial Sequence
<220> FEATURE:
<223> OTHER INFORMATION: Description of Artificial Sequence: Chimeric
      protein linker

<400> SEQUENCE: 55

Ala Met Gly Gly Gly Gly Ser Ala Met
  1               5

<210> SEQ ID NO 56
<211> LENGTH: 14
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 56

Ala Met Gly Gly Gly Gly Ser Gly Gly Gly Gly Ser Ala Met
  1               5                  10

<210> SEQ ID NO 57
<211> LENGTH: 19
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 57

Ala Met Gly Gly Gly Gly Ser Gly Gly Gly Ser Gly Gly Gly Gly
  1               5                  10                  15

Ser Ala Met

<210> SEQ ID NO 58
<211> LENGTH: 24
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 58

Ala Met Gly Gly Gly Gly Ser Gly Gly Gly Gly Ser Gly Gly Gly Gly
  1               5                  10                  15

Ser Gly Gly Gly Gly Ser Ala Met
                 20

<210> SEQ ID NO 59
<211> LENGTH: 29
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 59

Ala Met Gly Gly Gly Gly Ser Gly Gly Gly Gly Ser Gly Gly Gly Gly
  1               5                  10                  15

Ser Gly Gly Gly Gly Ser Gly Gly Gly Gly Ser Ala Met
                 20                  25

<210> SEQ ID NO 60
<211> LENGTH: 34
<212> TYPE: PRT
<213> ORGANISM: Artificial Sequence
```

```
<220> FEATURE:
<223> OTHER INFORMATION: Description of Artificial Sequence: Chimeric
      protein linker

<400> SEQUENCE: 60

Ala Met Gly Gly Gly Gly Ser Gly Gly Gly Gly Ser Gly Gly Gly Gly
  1               5                  10                  15

Ser Gly Gly Gly Gly Ser Gly Gly Gly Gly Ser Gly Gly Gly Gly Ser
                 20                  25                  30

Ala Met

<210> SEQ ID NO 61
<211> LENGTH: 39
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 61

Ala Met Gly Gly Gly Gly Ser Gly Gly Gly Gly Ser Gly Gly Gly Gly
  1               5                  10                  15

Ser Gly Gly Gly Gly Ser Gly Gly Gly Gly Ser Gly Gly Gly Gly Ser
                 20                  25                  30

Gly Gly Gly Gly Ser Ala Met
                 35

<210> SEQ ID NO 62
<211> LENGTH: 44
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 62

Ala Met Gly Gly Gly Gly Ser Gly Gly Gly Gly Ser Gly Gly Gly Gly
  1               5                  10                  15

Ser Gly Gly Gly Gly Ser Gly Gly Gly Gly Ser Gly Gly Gly Gly Ser
                 20                  25                  30

Gly Gly Gly Gly Ser Gly Gly Gly Gly Ser Ala Met
                 35                  40

<210> SEQ ID NO 63
<211> LENGTH: 49
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 63

Ala Met Gly Gly Gly Gly Ser Gly Gly Gly Gly Ser Gly Gly Gly Gly
  1               5                  10                  15

Ser Gly Gly Gly Gly Ser Gly Gly Gly Gly Ser Gly Gly Gly Gly Ser
                 20                  25                  30

Gly Gly Gly Gly Ser Gly Gly Gly Gly Ser Gly Gly Gly Gly Ser Ala
                 35                  40                  45

Met

<210> SEQ ID NO 64
<211> LENGTH: 54
```

```
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 64

Ala Met Gly Gly Gly Gly Ser Gly Gly Gly Gly Ser Gly Gly Gly Gly
 1               5                  10                  15

Ser Gly Gly Gly Gly Ser Gly Gly Gly Gly Ser Gly Gly Gly Gly Ser
            20                  25                  30

Gly Gly Gly Gly Ser Gly Gly Gly Ser Gly Gly Gly Gly Ser Gly
        35                  40                  45

Gly Gly Gly Ser Ala Met
    50

<210> SEQ ID NO 65
<211> LENGTH: 59
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 65

Ala Met Gly Gly Gly Gly Ser Gly Gly Gly Gly Ser Gly Gly Gly Gly
 1               5                  10                  15

Ser Gly Gly Gly Gly Ser Gly Gly Gly Gly Ser Gly Gly Gly Gly Ser
            20                  25                  30

Gly Gly Gly Gly Ser Gly Gly Gly Gly Ser Gly Gly Gly Gly Ser Gly
        35                  40                  45

Gly Gly Gly Ser Gly Gly Gly Gly Ser Ala Met
    50                  55

<210> SEQ ID NO 66
<211> LENGTH: 15
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 66

Gly Gly Gly Gly Ser Gly Gly Gly Gly Ser Gly Gly Gly Gly Ser
 1               5                  10                  15

<210> SEQ ID NO 67
<211> LENGTH: 20
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 67

Gly Gly Gly Gly Ser Gly Gly Gly Gly Ser Gly Gly Gly Gly Ser Gly
 1               5                  10                  15

Gly Gly Gly Ser
        20

<210> SEQ ID NO 68
<211> LENGTH: 25
<212> TYPE: PRT
<213> ORGANISM: Artificial Sequence
```

<220> FEATURE:
<223> OTHER INFORMATION: Description of Artificial Sequence: Chimeric
      protein linker

<400> SEQUENCE: 68

Gly Gly Gly Gly Ser Gly Gly Gly Gly Ser Gly Gly Gly Gly Ser Gly
 1               5                  10                  15

Gly Gly Gly Ser Gly Gly Gly Gly Ser
            20                  25

<210> SEQ ID NO 69
<211> LENGTH: 30
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 69

Gly Gly Gly Gly Ser Gly Gly Gly Gly Ser Gly Gly Gly Gly Ser Gly
 1               5                  10                  15

Gly Gly Gly Ser Gly Gly Gly Gly Ser Gly Gly Gly Gly Ser
            20                  25                  30

<210> SEQ ID NO 70
<211> LENGTH: 35
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 70

Gly Gly Gly Gly Ser Gly Gly Gly Gly Ser Gly Gly Gly Gly Ser Gly
 1               5                  10                  15

Gly Gly Gly Ser Gly Gly Gly Gly Ser Gly Gly Gly Gly Ser Gly Gly
            20                  25                  30

Gly Gly Ser
        35

<210> SEQ ID NO 71
<211> LENGTH: 40
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 71

Gly Gly Gly Gly Ser Gly Gly Gly Gly Ser Gly Gly Gly Gly Ser Gly
 1               5                  10                  15

Gly Gly Gly Ser Gly Gly Gly Gly Ser Gly Gly Gly Gly Ser Gly Gly
            20                  25                  30

Gly Gly Ser Gly Gly Gly Gly Ser
        35                  40

<210> SEQ ID NO 72
<211> LENGTH: 45
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 72

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
                20                  25                  30

Gly Gly Ser Gly Gly Gly Ser Gly Gly Gly Ser
            35                  40                  45

<210> SEQ ID NO 73
<211> LENGTH: 50
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 73

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
                20                  25                  30

Gly Gly Ser Gly Gly Gly Ser Gly Gly Gly Ser Gly Gly Gly
            35                  40                  45

Gly Ser
    50

<210> SEQ ID NO 74
<211> LENGTH: 55
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 74

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
                20                  25                  30

Gly Gly Ser Gly Gly Gly Ser Gly Gly Gly Ser Gly Gly Gly
            35                  40                  45

Gly Ser Gly Gly Gly Gly Ser
    50                  55

<210> SEQ ID NO 75
<211> LENGTH: 60
<212> TYPE: PRT
<213> ORGANISM: Artificial Sequence
<220> FEATURE:
<223> OTHER INFORMATION: Description of Artificial Sequence: Chimeric
      protein linker

<400> SEQUENCE: 75

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
                20                  25                  30

Gly Gly Ser Gly Gly Gly Ser Gly Gly Gly Ser Gly Gly Gly
            35                  40                  45

Gly Ser Gly Gly Gly Gly Ser Gly Gly Gly Ser
    50                  55                  60

```
<210> SEQ ID NO 76
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
acgactgcat ag                                                          12

<210> SEQ ID NO 77
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(12)

<400> SEQUENCE: 77 atg gac acc aaa                                                        12
Met Asp Thr Lys
  1

<210> SEQ ID NO 78
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(33)

<400> SEQUENCE: 78 acg act ggg cca aca ggg ccc atg gac acc aaa                            33
Thr Thr Gly Pro Thr Gly Pro Met Asp Thr Lys
  1               5                  10

<210> SEQ ID NO 79
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Met Asp Thr Lys
  1

<210> SEQ ID NO 80
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Thr Thr Gly Pro Thr Gly Pro Met Asp Thr Lys
  1               5                  10
```